(12) United States Patent
Hatakeyama et al.

(10) Patent No.: US 10,234,664 B2
(45) Date of Patent: Mar. 19, 2019

(54) MEDICAL STEREOMICROSCOPE OPTICAL SYSTEM AND MEDICAL OBSERVATION APPARATUS

(71) Applicant: SONY CORPORATION, Tokyo (JP)

(72) Inventors: Takeshi Hatakeyama, Chiba (JP); Sota Miyatani, Ishikawa (JP); Masaki Tamura, Kanagawa (JP); Atsushi Oohata, Tokyo (JP); Miki Sato, Kanagawa (JP)

(73) Assignee: Sony Corporation, Tokyo (JP)

( * ) Notice: Subject to any disclaimer, the term of this patent is extended or adjusted under 35 U.S.C. 154(b) by 0 days.

(21) Appl. No.: 15/512,252

(22) PCT Filed: Aug. 12, 2015

(86) PCT No.: PCT/JP2015/072868
§ 371 (c)(1),
(2) Date: Mar. 17, 2017

(87) PCT Pub. No.: WO2016/051969
PCT Pub. Date: Apr. 7, 2016

(65) Prior Publication Data
US 2017/0293129 A1    Oct. 12, 2017

(30) Foreign Application Priority Data
Oct. 3, 2014  (JP) ................................ 2014-204440

(51) Int. Cl.
*G02B 21/00*  (2006.01)
*G02B 23/24*  (2006.01)
(Continued)

(52) U.S. Cl.
CPC ....... *G02B 21/0012* (2013.01); *G02B 15/173* (2013.01); *G02B 21/025* (2013.01);
(Continued)

(58) Field of Classification Search
CPC ........ G02B 15/16; G02B 15/20; G02B 15/22; G02B 21/0012; G02B 21/18; G02B 21/20;
(Continued)

(56) References Cited

U.S. PATENT DOCUMENTS 5,438,456 A * 8/1995 Grinblat ................. G02B 21/22
                                                          359/368
5,691,850 A * 11/1997 Arisaka ................ G02B 25/001
                                                          359/644
(Continued)

FOREIGN PATENT DOCUMENTS

CN     102301268 A    12/2011
DE    102011007607 B3  8/2012
(Continued)

OTHER PUBLICATIONS

International Search Report and Written Opinion of PCT Application No. PCT/JP2015/072868, dated Sep. 15, 2015, 10 pages of English Translation and 09 pages of ISRWO.
(Continued)

*Primary Examiner* — Frank G Font
(74) *Attorney, Agent, or Firm* — Chip Law Group

(57) ABSTRACT

An image quality is improved although a medical stereomicroscope optical system and a medical observation apparatus are small and light. An objective optical system and a plurality of imaging optical systems are arranged in an order from an object side to an image side, and the imaging optical system has at least a single aspheric surface. Accordingly, a spherical aberration and a field curvature are improved, and the image quality is improved although the medical stereomicroscope optical system and a medical observation apparatus are small and light.

13 Claims, 15 Drawing Sheets

(51) Int. Cl.
*G02B 21/18* (2006.01)
*G02B 21/22* (2006.01)
*G02B 21/36* (2006.01)
*G02B 15/173* (2006.01)
*G02B 21/02* (2006.01)
*A61B 3/12* (2006.01)

(52) U.S. Cl.
CPC ............. *G02B 21/18* (2013.01); *G02B 21/22* (2013.01); *G02B 21/361* (2013.01); *G02B 23/2446* (2013.01); *A61B 3/12* (2013.01)

(58) Field of Classification Search
CPC .. G02B 21/22; G02B 21/361; G02B 23/2446; G02B 25/00; G02B 25/001; A61B 3/12
USPC ....... 359/376, 377, 379, 380, 419, 422, 643, 359/644, 656, 683, 687, 695, 739, 740, 359/766, 774
See application file for complete search history.

(56) References Cited

U.S. PATENT DOCUMENTS

| | | | |
|---|---|---|---|
| 5,933,275 A | 8/1999 | Igarashi | |
| 6,025,960 A | 2/2000 | Morooka | |
| 6,163,401 A | 12/2000 | Igarashi | |
| 6,674,582 B2* | 1/2004 | Kawasaki | G02B 21/025 359/380 |
| 2003/0165021 A1* | 9/2003 | Kawasaki | G02B 21/025 359/690 |
| 2012/0008194 A1 | 1/2012 | Mizuta et al. | |
| 2012/0262671 A1 | 10/2012 | Zünd | |
| 2013/0072917 A1* | 3/2013 | Kaschke | A61F 9/00736 606/6 |
| 2013/0279002 A1* | 10/2013 | Milman | G02B 9/12 359/407 |
| 2013/0314776 A1 | 11/2013 | Mizuta et al. | |

FOREIGN PATENT DOCUMENTS

| | | |
|---|---|---|
| EP | 2392959 A1 | 12/2011 |
| EP | 2472299 A2 | 7/2012 |
| EP | 2472300 A2 | 7/2012 |
| EP | 2472301 A2 | 7/2012 |
| JP | 09-113796 A | 5/1997 |
| JP | 9-113796 A | 5/1997 |
| JP | 11-183801 A | 7/1999 |
| JP | 2007-065651 A | 3/2007 |
| JP | 2011-221409 A | 11/2011 |
| JP | 2012-08361 A | 1/2012 |
| JP | 2012-008361 A | 1/2012 |
| JP | 2012-223577 A | 11/2012 |
| JP | 2013-047837 A | 3/2013 |
| JP | 2013-47837 A | 3/2013 |
| WO | 2010/087296 A1 | 8/2010 |

OTHER PUBLICATIONS

International Preliminary Report on Patentability of PCT Application No. PCT/JP2015/072868, dated Apr. 13, 2017, 11 pages of English Translation and 05 pages of IPRP.

* cited by examiner

FIG. 3
——— d LINE
------- g LINE
AZIMUTH: Y-DIRECTION     AZIMUTH: X-DIRECTION
ω=7.31°
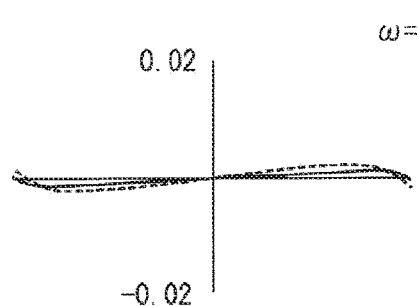 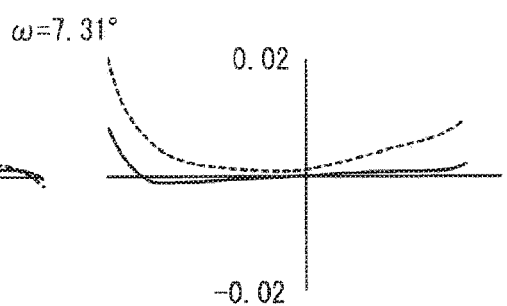
ω=-9.77°
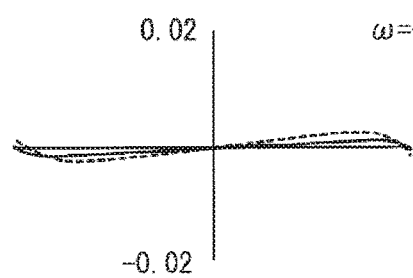 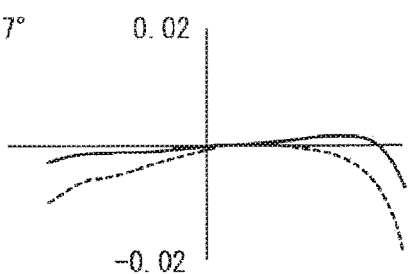
ω=-1.20°
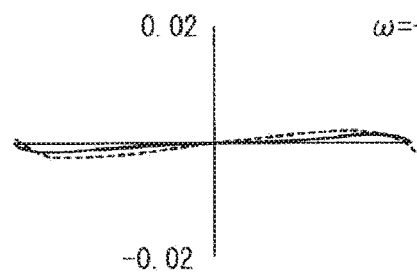 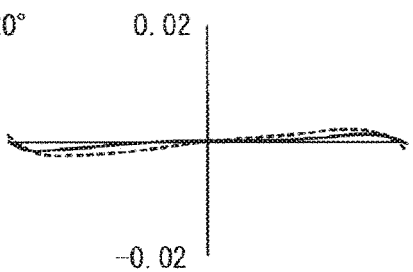

MEDICAL STEREOMICROSCOPE OPTICAL SYSTEM AND MEDICAL OBSERVATION APPARATUS

CROSS REFERENCE TO RELATED APPLICATIONS

This application is a U.S. National Phase of International Patent Application No. PCT/JP2015/072868 filed on Aug. 12, 2015, which claims priority benefit of Japanese Patent Application No. JP 2014-204440 filed in the Japan Patent Office on Oct. 3, 2014. Each of the above-referenced applications is hereby incorporated herein by reference in its entirety.

TECHNICAL FIELD

The present technology relates to a technical field of a medical stereomicroscope optical system having an objective optical system and a plurality of imaging optical systems arranged in an order from an object side to an image side and a medical observation apparatus.

CITATION LIST

Patent Document
Patent Document 1: Japanese Patent Application Laid-Open No. 2007-65651

BACKGROUND ART

A medical observation apparatus used for surgery, for example, a microscope for surgery has an important role to improve an efficiency of the surgery by enlarging and observing a surgical site by an operator (observer) such as a doctor at the time of the surgery.

As such a microscope for surgery, a stereomicroscope which can image a stereoscopic image has been widely used in recent years. For example, two imaging optical systems are provided in the stereomicroscope, and a stereoscopic image and video are obtained by using a parallax (for example, refer to Patent Document 1).

In the surgery using the medical observation apparatus, an operation has been widely performed in which an optical image enlarged by the stereomicroscope is photoelectrically converted by an image pickup element and an image and a video are projected on a display and stereographically observed. It is desirable that the image projected on the display have a high resolution. Therefore, it is required to improve an image quality and a resolution for the optical system.

The image quality of a television and a camera have been significantly improved in recent years. A high-resolution television camera system formed by combining a single-plate camera having over eight million pixels with a television having a resolution of about 2000 TV lines has been proposed. In an operation site for surgery and the like, the high-resolution television camera system has been desired to extend a procedure and improve safety. In this case, a resolution exceeding 2000 TV lines is required for the stereomicroscope optical system of the medical observation apparatus.

SUMMARY OF THE INVENTION

Problems to be Solved by the Invention

Most traditional stereomicroscope optical systems have been camera systems formed by being combined with a television having a resolution of about 1000 TV lines even when the traditional stereomicroscope optical system has a high resolution. Therefore, the resolution of the stereomicroscope optical system only satisfies 1000 TV lines. The high resolution of, for example, about 2000 TV lines required in the operation site for surgery has not been secured.

Also, when the stereomicroscope optical system has the resolution of about 2000 TV lines, since the optical system becomes large and heavy, a microscope unit and a mechanism part for holding the same become large. Therefore, there has been a problem in that the above causes decrease in the efficiency of the surgery and blocks a view of the observer.

A purpose of the present technology is to improve image qualities of a small and light medical stereomicroscope optical system and medical observation apparatus.

Solutions to Problems

Primarily, in a medical stereomicroscope optical system according to the present technology, an objective optical system and a plurality of imaging optical systems are arranged in an order from an object side to an image side, and the imaging optical system has at least a single aspheric surface.

According to this, a spherical aberration and a field curvature can be improved.

Second, in the medical stereomicroscope optical system according to the present technology, it is desirable that the objective optical system have a plurality of lens groups, and it is desirable to enable to change an operation distance by moving a part of lens groups of the objective optical system in an optical axis direction.

Accordingly, a focusing position and a convergence point can be constantly maintained to be fixed.

Third, in the medical stereomicroscope optical system according to the present technology, it is desirable that the imaging optical system include a plurality of lens groups, and it is desirable to enable to have a variable magnification as maintaining the operation distance by independently moving at least two or more lens groups of the imaging optical system in the optical axis direction.

Accordingly, it is possible to vary the magnification while a high resolution is maintained.

Fourth, in the medical stereomicroscope optical system according to the present technology, it is desirable that the imaging optical system include a first lens group having positive refractive power, a second lens group having negative refractive power, a third lens group having positive refractive power, and a fourth lens group having positive refractive power which are arranged in an order from the object side to the image side. When the image is magnified from a low magnification end to a high magnification end, it is desirable that the second lens group simply move from the object side to the image side and that the third lens group move to the image side along a convex track.

Accordingly, after a moving distance of the movable lens group is reduced, a magnification effect can be improved.

Fifth, in the medical stereomicroscope optical system according to the present technology, it is desirable that an aperture diaphragm be arranged in the imaging optical system and that the aperture diaphragm integrally move with the third lens group.

Accordingly, a light quantity variation at the time of magnifying the image can be reduced.

Sixth, in the medical stereomicroscope optical system according to the present technology, it is desirable that the imaging optical system include a first lens group having positive refractive power, a second lens group having negative refractive power, a third lens group having positive refractive power, a fourth lens group having negative refractive power, and a fifth lens group having positive refractive power which are arranged in an order from the object side to the image side. When the image is magnified from a low magnification end to a high magnification end, it is desirable that the second lens group simply move from the object side to the image side and that the fourth lens group move to the image side along a convex track.

Accordingly, after a moving distance of the movable lens group is reduced, a magnification effect can be improved.

Seventh, in the medical stereomicroscope optical system according to the present technology, it is desirable that the aperture diaphragm be arranged in the imaging optical system and that the aperture diaphragm be arranged between the second lens group and the third lens group.

Accordingly, an excellent balance between lens diameters of the lens group arranged on the object side than the aperture diaphragm and the lens group arranged on the image side can be secured.

Eighth, according to the medical stereomicroscope optical system of the present technology, in the imaging optical system, it is assumed that a field curvature amount of a meridional image surface at the low magnification end with the maximum image height in the horizontal direction be $\Delta FCL$, that a field curvature amount of a meridional image surface at the high magnification end be $\Delta FCH$, and that the maximum image height in the horizontal direction be IHH. At this time, it is desirable that the following conditional expressions (1) and (2) be satisfied.

$$0.012 < \Delta FCL/IHH < 0.050 \quad (1)$$

$$0.012 < \Delta FCH/IHH < 0.050 \quad (2)$$

Accordingly, correction of the field curvature of the entire optical system and miniaturization of the entire optical system can be realized without correcting the field curvatures of the objective optical system and the imaging optical system.

Ninth, in the medical stereomicroscope optical system according to the present technology, two imaging optical systems are provided, and the two imaging optical systems are eccentrically arranged relative to the objective optical system in the horizontal direction. It is assumed that an absolute value of an eccentricity quantity of the imaging optical system in the horizontal direction relative to the objective optical system be $\Delta DH$, that a F-number at the low magnification end of the entire optical system be FnoL, and that the maximum image height of the imaging optical system in the horizontal direction be IHH. At this time, it is desirable that the following conditional expression (3) is satisfied.

$$10 < \Delta DH \cdot FnoL/IHH < 40 \quad (3)$$

Accordingly, an excellent resolution and an appropriate stereoscopic effect can be obtained while the influence of the eccentric aberration caused by the eccentricity of the imaging optical system relative to the objective optical system is reduced.

Tenth, in the medical stereomicroscope optical system according to the present technology, it is desirable that the imaging optical system include a first lens group having positive refractive power, a second lens group having negative refractive power, a third lens group having positive refractive power, and a fourth lens group having positive refractive power which are arranged in an order from the object side to the image side. Also, it is desirable that the first lens group have an aspheric surface.

Accordingly, the spherical aberration at the high magnification end can be satisfactorily corrected.

Eleventh, in the medical stereomicroscope optical system according to the present technology, it is desirable that the imaging optical system include a first lens group having positive refractive power, a second lens group having negative refractive power, a third lens group having positive refractive power, and a fourth lens group having positive refractive power which are arranged in an order from the object side to the image side. Also, it is desirable that the third lens group have an aspheric surface.

Accordingly, the spherical aberration at the low magnification end can be satisfactorily corrected.

Twelfth, in the medical stereomicroscope optical system according to the present technology, it is desirable that the imaging optical system include the first lens group having positive refractive power, the second lens group having negative refractive power, the third lens group having positive refractive power, the fourth lens group having negative refractive power, and a fifth lens group having positive refractive power which are arranged in an order from the object side to the image side. Also, it is desirable that the first lens group have an aspheric surface.

Accordingly, the spherical aberration at the high magnification end can be satisfactorily corrected.

Thirteenth, in the medical stereomicroscope optical system according to the present technology, it is desirable that the imaging optical system include the first lens group having positive refractive power, the second lens group having negative refractive power, the third lens group having positive refractive power, the fourth lens group having negative refractive power, and the fifth lens group having positive refractive power which are arranged in an order from the object side to the image side. Also, it is desirable that the third lens group have an aspheric surface.

Accordingly, the spherical aberration at the low magnification end can be satisfactorily corrected.

In the medical observation apparatus according to the present technology, the objective optical system and the plurality of imaging optical systems are arranged in an order from the object side to the image side and the image pickup element is provided which converts the optical image formed by the objective optical system and the plurality of imaging optical systems into an electrical signal and the imaging optical system has at least a single aspheric surface.

According to this, a spherical aberration and a field curvature can be improved.

Effects of the Invention

According to the present technology, a spherical aberration and a field curvature can be improved, and an image quality can be improved although the size is small and the weight is light.

Here, effects described herein are only exemplary and not limited to these. Also, there may be an additional effect.

BRIEF DESCRIPTION OF DRAWINGS

FIG. 2 is a diagram of longitudinal aberrations (spherical aberration, astigmatism aberration, and distortion aberration) at the time of focusing with an operation distance of 405 mm in a low magnification state.

FIG. 3 is a diagram of a lateral aberration (comatic aberration) at the time of focusing with an operation distance of 405 mm in a low magnification state of numerical value example 1.

FIG. 9 is a diagram of longitudinal aberrations (spherical aberration, astigmatism aberration, and distortion aberration) at the time of focusing with an operation distance of 405 mm in the low magnification state.

MODE FOR CARRYING OUT THE INVENTION

Figure 1:
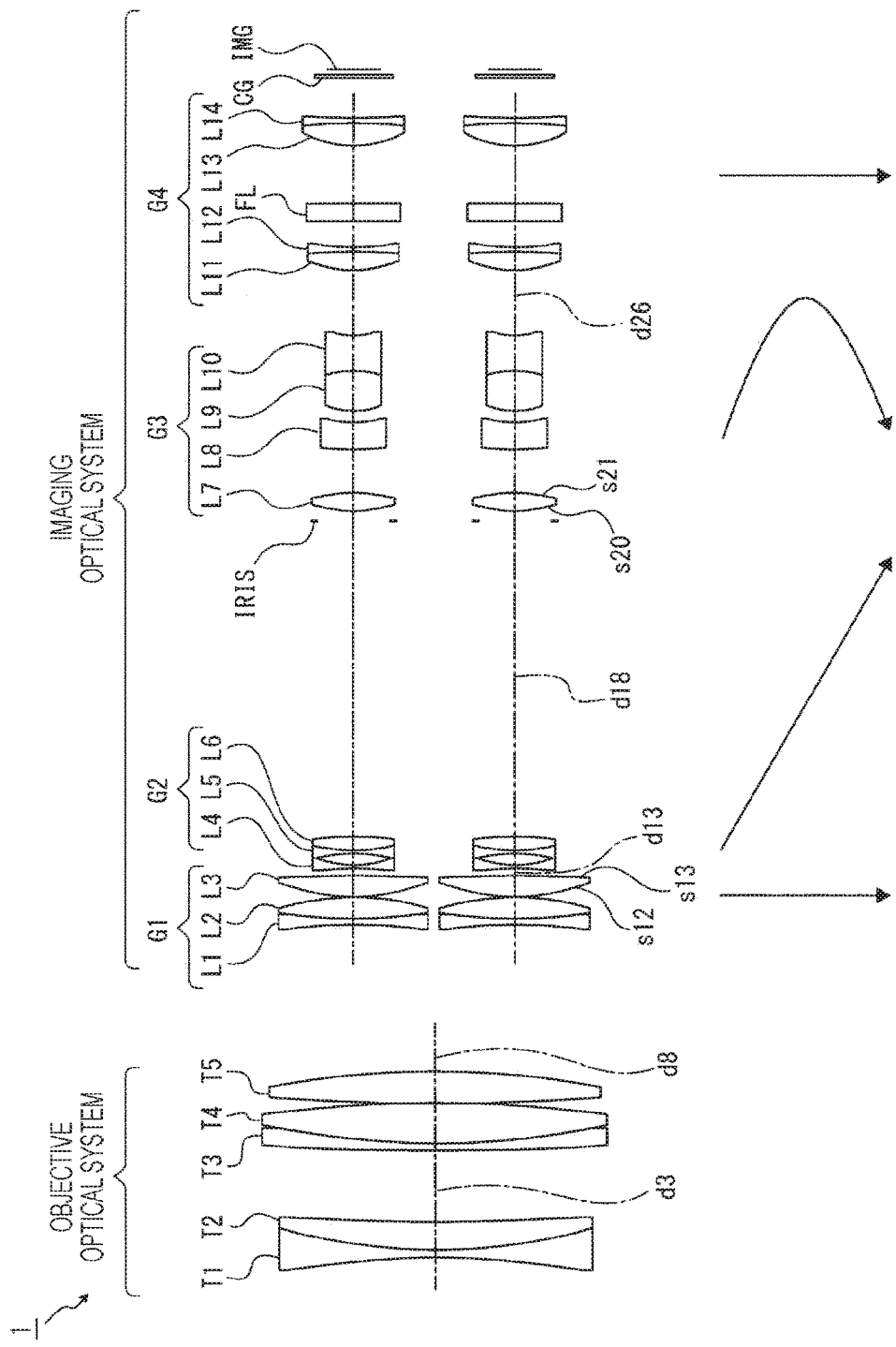
FIG. 1 is a diagram of a lens structure according to a first embodiment of a medical stereomicroscope optical system of the present technology.

Embodiments for carrying out the present technology are described below with reference the attached drawings.

Structure of Medical Stereomicroscope Optical System

In a medical stereomicroscope optical system according to the present technology, an objective optical system and a plurality of imaging optical systems are arranged in an order from the object side to the image side, and the imaging optical system has at least a single aspheric surface.

Since the imaging optical system has the aspheric surface, a spherical aberration and a field curvature can be improved, and an image quality of the small and light medical stereomicroscope optical system can be improved.

In the medical stereomicroscope optical system according to one embodiment of the present technology, it is desirable that the objective optical system include a plurality of lens groups, and it is preferable to enable to change the operation distance by moving a part of the lens groups in the objective optical system in an optical axis direction.

The operation distance can be changed by moving a part of the lens groups of the objective optical system in the optical axis direction in this way, and accordingly, a focusing position and a convergence point can be constantly maintained to be fixed, and a stereoscopic image which is comfortably observed can be provided.

In the medical stereomicroscope optical system according to one embodiment of the present technology, it is desirable that the imaging optical system include a plurality of lens groups, and it is desirable to have a variable magnification as maintaining the operation distance by independently moving at least two or more lens groups of the imaging optical system in the optical axis direction.

The medical stereomicroscope optical system can have the variable magnification as maintaining the operation distance by independently moving at least two or more lens groups of the imaging optical system in the optical axis direction in this way, and accordingly, a view range can be freely changed while keeping resolution of the image high.

In the medical stereomicroscope optical system according to one embodiment of the present technology, it is desirable that the imaging optical system include a first lens group having positive refractive power, a second lens group having negative refractive power, a third lens group having positive refractive power, and a fourth lens group having positive refractive power which are arranged in an order from the object side to the image side. When the image is magnified from a low magnification end to a high magnification end, it is desirable that the second lens group simply move from the object side to the image side and that the third lens group move to the image side along a convex track.

A large magnification effect can be obtained by simply moving the second lens group having the negative refractive power to the image side as having the lateral magnification so as to across the same magnification. Also, by moving the third lens group having the positive refractive power to the image side along the convex track, a change of an image point position according to the movement of the second lens group can be corrected, and a small magnification effect can be obtained.

On the other hand, although the change of the image point position can be corrected by moving the fourth lens group having the positive refractive power, a moving amount is increased than a case where the third lens group is moved. Also, the medical stereomicroscope optical system becomes larger. Therefore, this is not preferable.

Accordingly, the medical stereomicroscope optical system has four groups and has a structure in which the second lens group simply moves from the object side to the image side and the third lens group moves to the image side along the convex track. This can increase the magnification effect while reducing the moving distance of movable lens group, and the medical stereomicroscope optical system can be miniaturized.

In the medical stereomicroscope optical system according to one embodiment of the present technology, it is desirable that an aperture diaphragm be arranged in the imaging optical system and the aperture diaphragm integrally move with the third lens group in the above four-group structure imaging optical system.

When the aperture diaphragm is fixed at a position of the high magnification end, the height of the main light beam of an off-axis light beam which passes through the third lens group on the low magnification side becomes high. Therefore, the lens diameter of the third lens group increases, and this prevents the miniaturization.

Therefore, according to the structure in which the aperture diaphragm integrally moves with the third lens group, a change of the light quantity at the time of varying the magnification can be prevented, and the medical stereomicroscope optical system can be miniaturized.

In the medical stereomicroscope optical system according to one embodiment of the present technology, it is desirable that the imaging optical system includes the first lens group having the positive refractive power, the second lens group having the negative refractive power, the third lens group having the positive refractive power, the fourth lens group having the negative refractive power, and a fifth lens group having positive refractive power which are arranged in an order from the object side to the image side. Also, it is desirable that the second lens group simply move from the object side to the image side and the fourth lens group move to the image side along the convex track when the magnification is varied from the low magnification end to the high magnification end.

A large magnification effect can be obtained by simply moving the second lens group having the negative refractive power to the image side as having the lateral magnification so as to across the same magnification. Also, the change of the image point position according to the movement of the second lens group can be corrected with a small moving amount by moving the fourth lens group which has been arranged next to the fixed third lens group having the positive refractive power to the image side along the convex track.

On the other hand, the change of the image point position can be corrected by moving the fifth lens group having the positive refractive power. However, the moving amount is increased than a case where the fourth lens group is moved, and the medical stereomicroscope optical system becomes larger. Therefore, this is not preferable.

Accordingly, the medical stereomicroscope optical system has five groups and has a structure in which the second lens group simply moves from the object side to the image side and the fourth lens group moves to the image side along the convex track. This can increase the magnification effect while reducing the moving distance of movable lens group, and the medical stereomicroscope optical system can be miniaturized.

In the medical stereomicroscope optical system according to one embodiment of the present technology, it is desirable that the aperture diaphragm be arranged in the imaging optical system and the aperture diaphragm be arranged between the second lens group and the third lens group in the above five-group structure imaging optical system.

The aperture diaphragm is arranged between the second lens group and the third lens group in this way so that the aperture diaphragm is fixed between the second lens group and the third lens group. Therefore, the lens diameters of the lens group arranged on the object side than the aperture diaphragm and the lens group arranged on the image side are well-balanced, and the medical stereomicroscope optical system can be miniaturized.

According to the medical stereomicroscope optical system according to one embodiment of the present technology, in the imaging optical system, it is assumed that a field curvature amount of a meridional image surface at the low magnification end with the maximum image height in the horizontal direction be $\Delta FCL$, that a field curvature amount of a meridional image surface at the high magnification end be $\Delta FCH$, and that the maximum image height in the horizontal direction be IHH. At this time, it is desirable that the following conditional expressions (1) and (2) be satisfied.

$$0.012 < \Delta FCL/IHH < 0.050 \tag{1}$$

$$0.012 < \Delta FCH/IHH < 0.050 \tag{2}$$

The conditional expressions (1) and (2) respectively specify a ratio of the field curvature amount of the meridional image surface at the low magnification end of the imaging optical system relative to the maximum image height in the horizontal direction and a ration of the field curvature amount of the meridional image surface at the high magnification end relative to the maximum image height in the horizontal direction.

When the value falls below the lower limit values of the conditional expressions (1) and (2), since it is necessary to sufficiently correct the field curvature in the objective optical system and the imaging optical system, the objective optical system and the imaging optical system become large.

Conversely, when the value exceeds the upper limit values of the conditional expressions (1) and (2), since the variation of the field curvature generated in the imaging optical system becomes too large, it is difficult to satisfactorily correct the field curvature as a whole, and the image quality is deteriorated.

Therefore, according to the structure cancelling the minus field curvature of the meridional image surface generated in the objective optical system by satisfying the conditional expressions (1) and (2), the field curvature can be sufficiently corrected, and the medical stereomicroscope optical system can be miniaturized.

Also, in the medical stereomicroscope optical system, to obtain an excellent optical performance, it is desirable that the following conditional expressions (1)' and (2)' be satisfied.

$$0.020 < \Delta FCL/IHH < 0.040 \tag{1'}$$

$$0.020 < \Delta FCH/IHH < 0.040 \tag{2'}$$

The medical stereomicroscope optical system satisfies the conditional expressions (1)' and (2)' so that the field curvature can be more sufficiently corrected and the medical stereomicroscope optical system can be more miniaturized.

In the medical stereomicroscope optical system according to one embodiment of the present technology, two imaging optical systems are provided, and the two imaging optical systems are eccentrically arranged relative to the objective optical system in the horizontal direction. It is assumed that an absolute value of an eccentricity quantity of the imaging optical system in the horizontal direction relative to the objective optical system be $\Delta DH$, that a F-number at the low magnification end of entire optical system be FnoL, and that the maximum image height of the imaging optical system in the horizontal direction be IHH. At this time, it is desirable that the following conditional expression (3) is satisfied.

$$10 < \Delta DH \cdot FnoL/IHH < 40 \qquad (3)$$

The conditional expression (3) specifies a relation between the eccentricity quantity of the imaging optical system in the horizontal direction relative to the objective optical system, the F-number of the entire optical system, and a size of an image pickup element.

When the value falls below the lower limit value of the conditional expression (3), an influence of the eccentric aberration caused by the eccentricity of the imaging optical system on the objective optical system becomes large, and the image quality is deteriorated. In addition, the depth of field becomes too narrow, and a stereoscopic effect is lacked. It becomes difficult to comfortably perform stereoscopic observation of a surgical site.

Conversely, when the value exceeds the upper limit value of the conditional expression (3), it is difficult to obtain an excellent image quality due to a diffraction limit, and the stereoscopic effect becomes too large. Then, it becomes difficult to comfortably perform stereoscopic observation of the surgical site.

Therefore, by satisfying the conditional expression (3), the influence of the eccentric aberration caused by the eccentricity of the imaging optical system on the objective optical system decreases. While having an excellent resolution and an appropriate stereoscopic effect, the medical stereomicroscope optical system can obtain the depth of field as deep as possible. Especially, regarding the resolution, about 2000 TV lines of the resolution can be secured.

Also, in the medical stereomicroscope optical system, to obtain an excellent optical performance, it is desirable that the conditional expression (3)' be satisfied.

$$15 < \Delta DH \cdot FnoL/IHH < 30 \qquad (3)'$$

The medical stereomicroscope optical system satisfies the conditional expression (3)' so that the influence of the eccentric aberration of the eccentricity of the imaging optical system on the objective optical system becomes smaller. While having a more excellent resolution and a more appropriate stereoscopic effect, the medical stereomicroscope optical system can obtain the depth of field as deep as possible.

In the medical stereomicroscope optical system according to one embodiment of the present technology, it is desirable that the imaging optical system include a first lens group having positive refractive power, a second lens group having negative refractive power, a third lens group having positive refractive power, and a fourth lens group having positive refractive power which are arranged in an order from the object side to the image side. Also, it is desirable that the first lens group have an aspheric surface.

The first lens group has a large luminous flux diameter. The first lens group has a structure including the aspheric surface so that the spherical aberration at the high magnification end can be satisfactorily corrected, and a high resolution can be secured.

In the medical stereomicroscope optical system according to one embodiment of the present technology, it is desirable that the imaging optical system include a first lens group having positive refractive power, a second lens group having negative refractive power, a third lens group having positive refractive power, and a fourth lens group having positive refractive power which are arranged in an order from the object side to the image side. Also, it is desirable that the third lens group have an aspheric surface.

The third lens group has a large luminous flux diameter. The third lens group has a structure including the aspheric surface so that the spherical aberration at the low magnification end can be satisfactorily corrected, and a high resolution can be secured.

In the medical stereomicroscope optical system according to one embodiment of the present technology, it is desirable that the imaging optical system include the first lens group having positive refractive power, the second lens group having negative refractive power, the third lens group having positive refractive power, the fourth lens group having negative refractive power, and the fifth lens group having positive refractive power which are arranged in an order from the object side to the image side. Also, it is desirable that the first lens group have an aspheric surface.

The first lens group has a large luminous flux diameter. The first lens group has a structure including the aspheric surface so that the spherical aberration at the high magnification end can be satisfactorily corrected, and a high resolution can be secured.

In the medical stereomicroscope optical system according to one embodiment of the present technology, it is desirable that the imaging optical system include the first lens group having positive refractive power, the second lens group having negative refractive power, the third lens group having positive refractive power, the fourth lens group having negative refractive power, and the fifth lens group having positive refractive power which are arranged in an order from the object side to the image side. Also, it is desirable that the third lens group have an aspheric surface.

The third lens group has a large luminous flux diameter. The third lens group has a structure including the aspheric surface so that the spherical aberration at the low magnification end can be satisfactorily corrected, and a high resolution can be secured.

Also, the spherical aberration and the field curvature can be further improved by forming the aspheric surface on the lens group other than the first lens group and the third lens group. However, in consideration of manufacturing cost of an aspheric surface lens and a difficulty in molding, the most effective method is to arrange a single aspheric surface lens on the first lens group or the third lens group.

EMBODIMENTS

Next, a specific embodiment of the medical stereomicroscope optical system according to the present technology and a numerical value example in which concrete numerical values are applied to the embodiment are described with reference to the drawings and tables.

In addition, meanings of references indicated in the tables and descriptions below are described as follows.

The reference "si" indicates a i-th surface from the object side, and the reference "ri" indicates a curvature of radius of the i-th surface from the object side. The reference "di" indicates an axial surface distance between the i-th surface and the i+1-th surface (thickness of center of lens or air gap), the reference "ni" indicates a refractive index of a d-line (wavelength 587.6 nm) of a material of the lens having the i-th surface, and the reference "vi" indicates the Abbe's number at the d-line of the material of the lens having the i-th surface.

Regarding the reference "ri", the reference "*" indicates that the surface is an aspheric surface, and the reference "INFINITY" indicates that the surface is a plane surface. Regarding the reference "di", "variable" indicates that the distance is a variable distance.

It is assumed that an amount of eccentricity be that from the center of an original point of the optical system to the surface top position of the surface (X-direction and Y-direction are respectively indicated as X and Y). The X-direction is a direction in which the two imaging optical systems are arranged (horizontal direction), and the Y-direction is perpendicular to both the optical axis direction and the X-direction.

The reference "K" indicates a conic constant, and the references "A4", "A6", "A8", and "A10" respectively indicate a fourth order, sixth order, eighth order, and tenth order aspheric surface coefficients.

The reference "magnification" indicates an image forming magnification, and the reference "Fno" indicates a F-number. The reference "IH" indicates a height of an image of the imaging optical system, and the reference "ω" indicates a half angle of view.

Some lenses used in each numerical value example have lens surfaces formed as an aspheric surface.

The aspheric surface shape is defined by the following mathematical formula 1 when it is assumed that a vertex of the surface be an original point, that the optical axis direction be a Z-axis, and that the height perpendicular to the optical axis be h.

$$Z = \frac{h^2/R}{1 + \sqrt{1-(1+K)h^2/R^2}} + \Sigma A_i h^i \quad \text{[Mathematical Formula 1]}$$

At this time, it is assumed that Ai be the i-th order aspheric surface coefficient, that R be the curvature of radius, and that K be the conic constant.

In addition, in each Tables indicating the aspheric surface coefficient below, the reference "E-n" indicates an exponential notation having ten as a base, that is, "minus n-th power of 10". For example, "0.12345E-05" indicates "0.12345× (minus fifth power of 10)".

In a medical stereomicroscope optical system 1 and 2 according to the first and second embodiments described below, an objective optical system and two imaging optical systems are arranged in an order from the object side to the image side, and each imaging optical system has at least a single aspheric surface.

First Embodiment

FIG. 1 is a diagram of a lens structure of a medical stereomicroscope optical system 1 according to a first embodiment of the present technology.

A variable magnification ratio of the medical stereomicroscope optical system 1 is set to be about 6 times.

The objective optical system includes a compound lens formed by joining a biconcave negative lens T1 to a meniscus positive lens T2 having a convex faced to the object side, a compound lens formed by joining a meniscus negative lens T3 having a convex faced to the object side to a biconvex positive lens T4, and a biconvex positive lens T5 which are arranged in an order from the object side to the image side.

An operation distance can be changed by integrally moving the negative lens T3, the positive lens T4, and the positive lens T5 in an optical axis direction.

In the imaging optical system, an imaging optical system for a left eye is arranged at a position 10 mm eccentric relative to an optical axis of the objective optical system in an X-direction, and an imaging optical system for a right eye is arranged at a position 10 mm eccentric relative to the optical axis in the X-direction.

The imaging optical system includes a first lens group G1 having positive refractive power, a second lens group G2 having negative refractive power, a third lens group G3 having positive refractive power, and a fourth lens group G4 having positive refractive power which are arranged in an order from the object side to the image side. The first lens group G1 and the fourth lens group G4 are fixed lens groups which are fixed in the optical axis direction, and the second lens group G2 and the third lens group G3 are movable lens group which are moved in the optical axis direction.

The first lens group G1 includes a compound lens formed by joining a biconcave negative lens L1 to a biconvex positive lens L2 and a biconvex positive lens L3 arranged in an order from the object side to the image side.

Both surfaces of the positive lens L3 are formed as aspheric surfaces. The positive lens L3 is the aspheric surface lens so as to affect correction of a spherical aberration in a high magnification state.

The second lens group G2 includes a biconcave negative lens L4 and a compound lens formed by joining a biconcave negative lens L5 to a biconvex positive lens L6 which are arranged in an order from the object side to the image side.

The second lens group G2 simply moves from the object side to the image side when a magnification varies from the low magnification end to the high magnification end.

The third lens group G3 includes a biconvex positive lens L7, a meniscus negative lens L8 having a convex faced to the object side, and a compound lens formed by joining a biconvex positive lens L9 to a biconcave negative lens L10 which are arranged in an order from the object side to the image side.

Both surfaces of the positive lens L7 are formed as aspheric surfaces. The positive lens L7 is the aspheric surface lens so as to affect correction of a spherical aberration in a low magnification state.

The third lens group G3 moves to the image side along a convex track when the magnification varies from the low magnification end to the high magnification end.

An aperture diaphragm IRIS is arranged between the second lens group G2 and the third lens group G3. The aperture diaphragm IRIS is integrally moved with the third lens group G3 in the optical axis direction when the magnification varies.

The fourth lens group G4 includes a compound lens formed by joining a biconvex positive lens L11 to a biconcave negative lens L12 and a compound lens formed by joining a biconvex positive lens L13 to a biconcave negative lens L14 which are arranged in an order from the object side to the image side.

A filter block FL is arranged between the negative lens L12 and the positive lens L13. On the image side of the fourth lens group G4, a cover glass CG and an image surface (image pickup element) IMG are arranged in an order from the object side to the image side.

In Table 1, lens data of the numerical value example 1 obtained by applying concrete numerical values to the medical stereomicroscope optical system 1 according to the first embodiment is illustrated.

TABLE 1

OPERATION DISTANCE (WD): 405 mm

| si | ri | di | ni | vi |
|---|---|---|---|---|
| (OBJECTIVE OPTICAL SYSTEM) | | | | |
| s1 | −97.0441 | 1.000 | 1.72000 | 43.7 |
| s2 | 72.8844 | 3.400 | 1.84666 | 23.8 |
| s3 | 318.0835 | VARIABLE | | |
| s4 | 265.1204 | 1.000 | 1.84666 | 23.8 |
| s5 | 98.2170 | 5.000 | 1.49700 | 81.6 |
| s6 | −165.5732 | 0.200 | | |
| s7 | 375.1031 | 3.920 | 1.53172 | 48.8 |
| s8 | −101.7261 | VARIABLE | | |
| (IMAGING OPTICAL SYSTEM) | | | | |
| s9 | −67.4611 | 0.700 | 1.80420 | 46.5 |
| s10 | 58.1035 | 2.730 | 1.49700 | 81.6 |
| s11 | −31.3240 | 0.150 | | |
| s12 | 25.6701 | 2.400 | 1.49710 | 81.6 |
| s13 | −365.8354 | VARIABLE | | |
| s14 | −70.7924 | 0.450 | 1.59349 | 67.0 |
| s15 | 16.7186 | 1.400 | | |
| s16 | −19.6263 | 0.400 | 1.59282 | 68.6 |
| s17 | 19.6263 | 1.378 | 1.80610 | 33.3 |
| s18 | −125.8388 | VARIABLE | | |
| s19 | INFINITY | 1.150 | | APERTURE DIAPHRAGM |
| s20 | 14.9033 | 2.200 | 1.49710 | 81.6 |
| s21 | −27.6532 | 5.568 | | |
| s22 | 42.5894 | 3.620 | 1.88100 | 40.1 |
| s23 | 17.4311 | 1.300 | | |
| s24 | 7.9084 | 4.982 | 1.48749 | 70.4 |
| s25 | −12.7944 | 4.536 | 1.88300 | 40.8 |

TABLE 1-continued

OPERATION DISTANCE (WD): 405 mm

| si | ri | di | ni | vi |
|---|---|---|---|---|
| s26 | 7.6698 | VARIABLE | | |
| s27 | 14.0573 | 2.398 | 1.61800 | 63.4 |
| s28 | −49.9432 | 0.500 | 1.83400 | 37.3 |
| s29 | 28.0631 | 3.295 | | |
| s30 | INFINITY | 2.300 | 1.51633 | 64.1 |
| s31 | INFINITY | 7.334 | | |
| s32 | 12.8886 | 2.941 | 1.74077 | 27.8 |
| s33 | −39.4963 | 0.500 | 1.88100 | 40.1 |
| s34 | 64.3515 | 5.219 | | |
| s35 | INFINITY | 0.500 | 1.51680 | 64.2 |
| s36 | INFINITY | | | |

Amount of Eccentricity of Imaging Optical System Relative to Objective Optical System $X=10.00$ $Y=0.00$ In the medical stereomicroscope optical system 1, both surfaces of the positive lens L3 in the first lens group G1 (twelfth and thirteenth surfaces) and both surfaces of the positive lens L7 in the third lens group G3 (twentieth and twenty-first surfaces) are formed as aspheric surfaces. The fourth order, sixth order, eighth order, and tenth order aspheric surface coefficients A4, A6, A8, and A10 of the aspheric surface in the numerical value example 1 are indicated in Table 2 together with the conic constant K.

TABLE 2

| si | K | A4 | A6 | A8 | A10 |
|---|---|---|---|---|---|
| 12 | 0.0000 | −4.91039E−06 | 3.06772E−09 | 0.00000E+00 | 0.00000E−00 |
| 13 | 0.0000 | −1.36258E−06 | 9.30800E−09 | 0.00000E−00 | 0.00000E−00 |
| 20 | 0.0000 | −1.52646E−05 | −7.31920E−07 | −2.81332E−09 | 0.00000E−00 |
| 21 | 0.0000 | 4.67059E−05 | −9.36204E−07 | 1.27128E−09 | 0.00000E−00 |

Variable intervals of the operation distances in the low magnification state, the intermediate magnification, and the high magnification state in the numerical value example 1 are indicated in Table 3 together with the magnification and the F-number Fno.

TABLE 3

| | LOW MAGNIFICATION END | INTERMEDIATE MAGNIFICATION | HIGH MAGNIFICATION END (1) | HIGH MAGNIFICATION END (2) | HIGH MAGNIFICATION END (3) |
|---|---|---|---|---|---|
| OPERATION DISTANCE | 405.00 | 405.00 | 405.00 | 205.00 | 605.00 |
| MAGNIFICATION | 0.053 | 0.129 | 0.316 | 0.510 | 0.229 |
| Fno | 7.00 | 7.00 | 9.00 | 8.98 | 9.02 |
| d3 | 8.971 | 8.971 | 8.971 | 25.671 | 1.490 |
| d8 | 18.482 | 18.482 | 18.482 | 1.783 | 25.964 |
| d13 | 1.200 | 19.279 | 24.311 | 24.311 | 24.311 |
| d18 | 40.278 | 24.522 | 1.000 | 1.000 | 1.000 |
| d26 | 8.099 | 5.775 | 24.265 | 24.265 | 24.265 |

Figure 2:
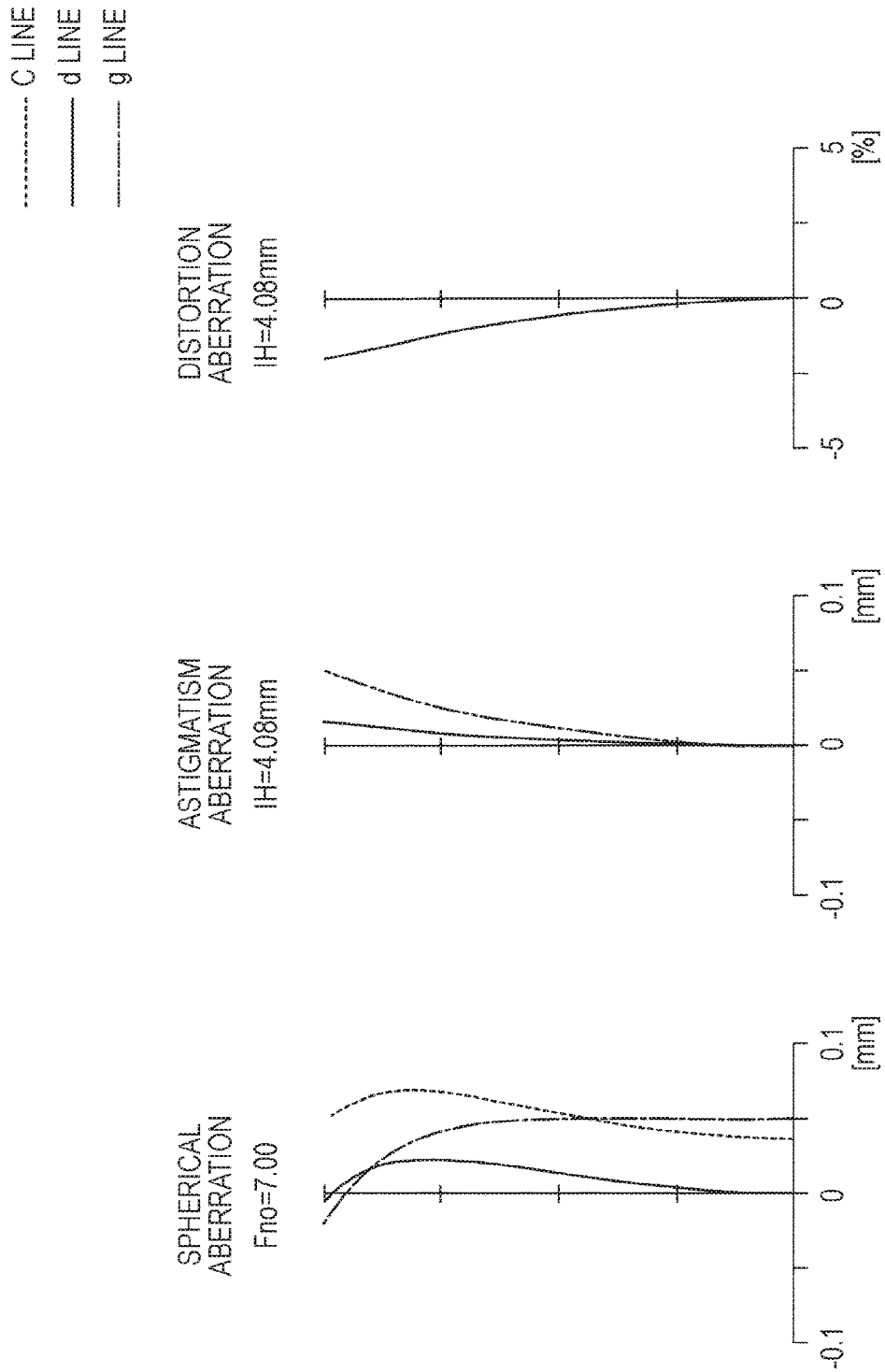
FIG. 2 illustrates aberrations in the numerical value example 1 in which concrete numerical values are applied to the first embodiment together with FIGS. 3 to 7.
Figure 4:
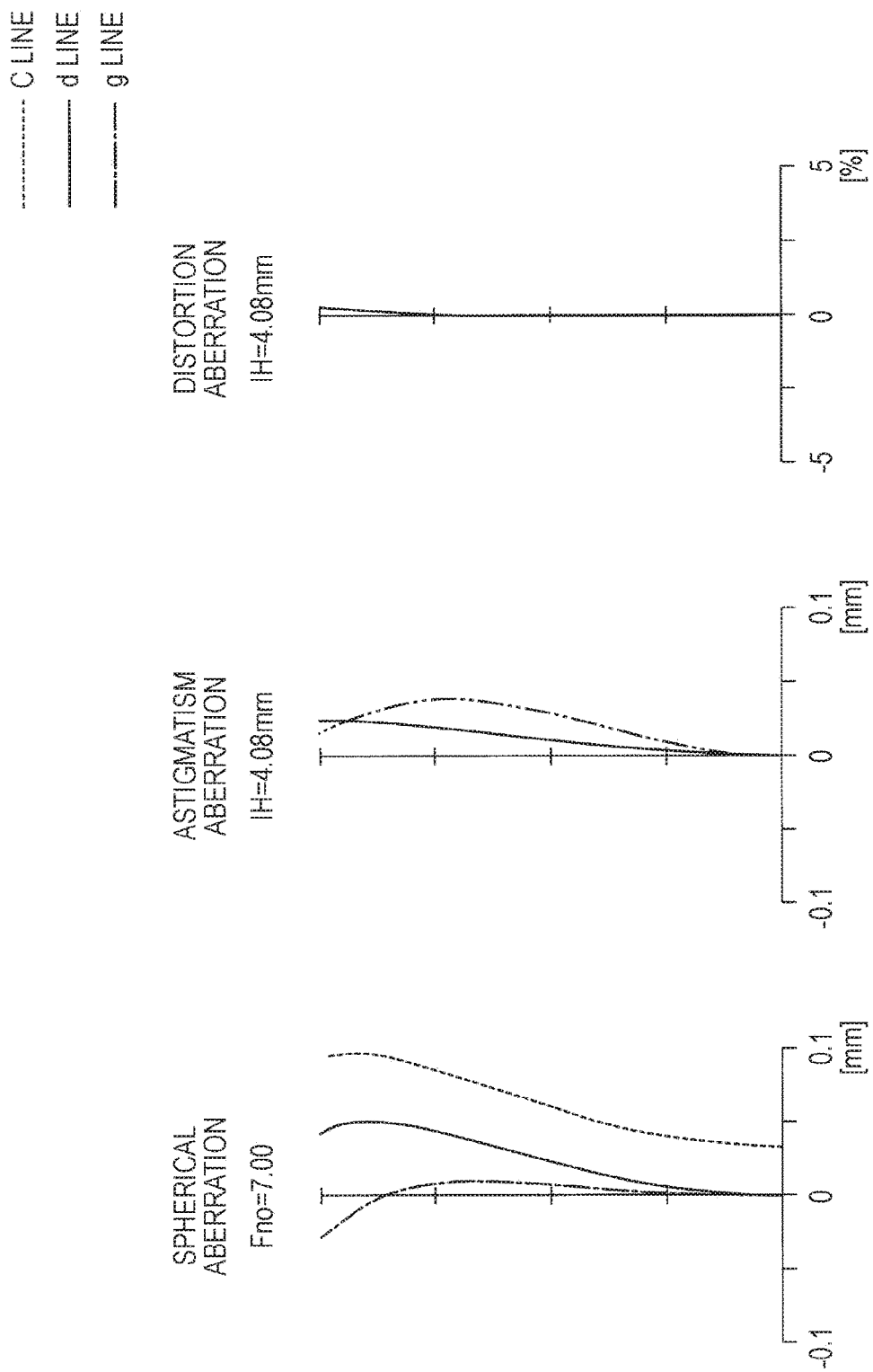
FIG. 4 is a diagram of longitudinal aberrations (spherical aberration, astigmatism aberration, and distortion aberration) at the time of focusing with an operation distance of 405 mm in an intermediate magnification state of the numerical value example 1.
Figure 5:
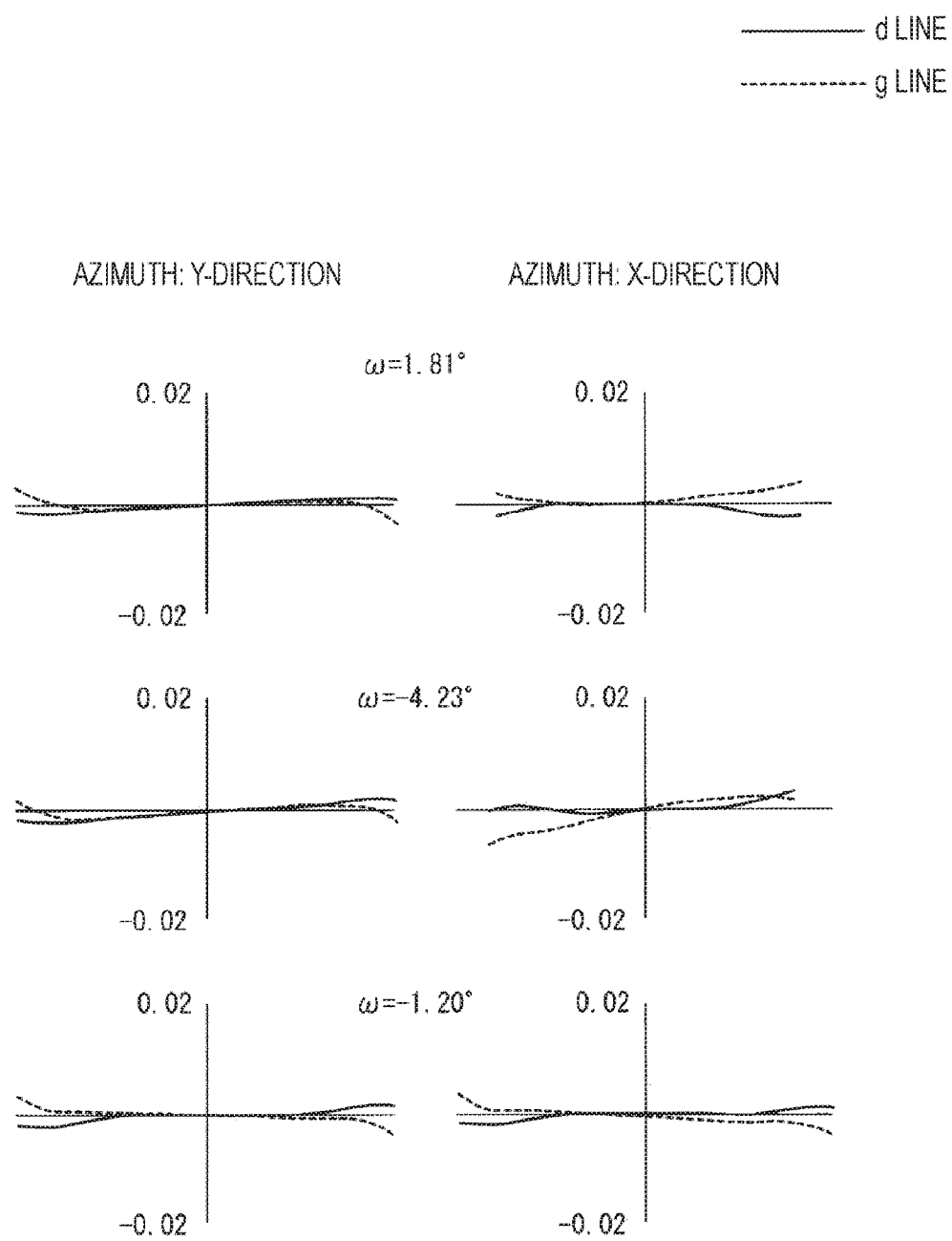
FIG. 5 is a diagram of a lateral aberration (comatic aberration) at the time of focusing with an operation distance of 405 mm in the intermediate magnification state of the numerical value example 1.
Figure 6:
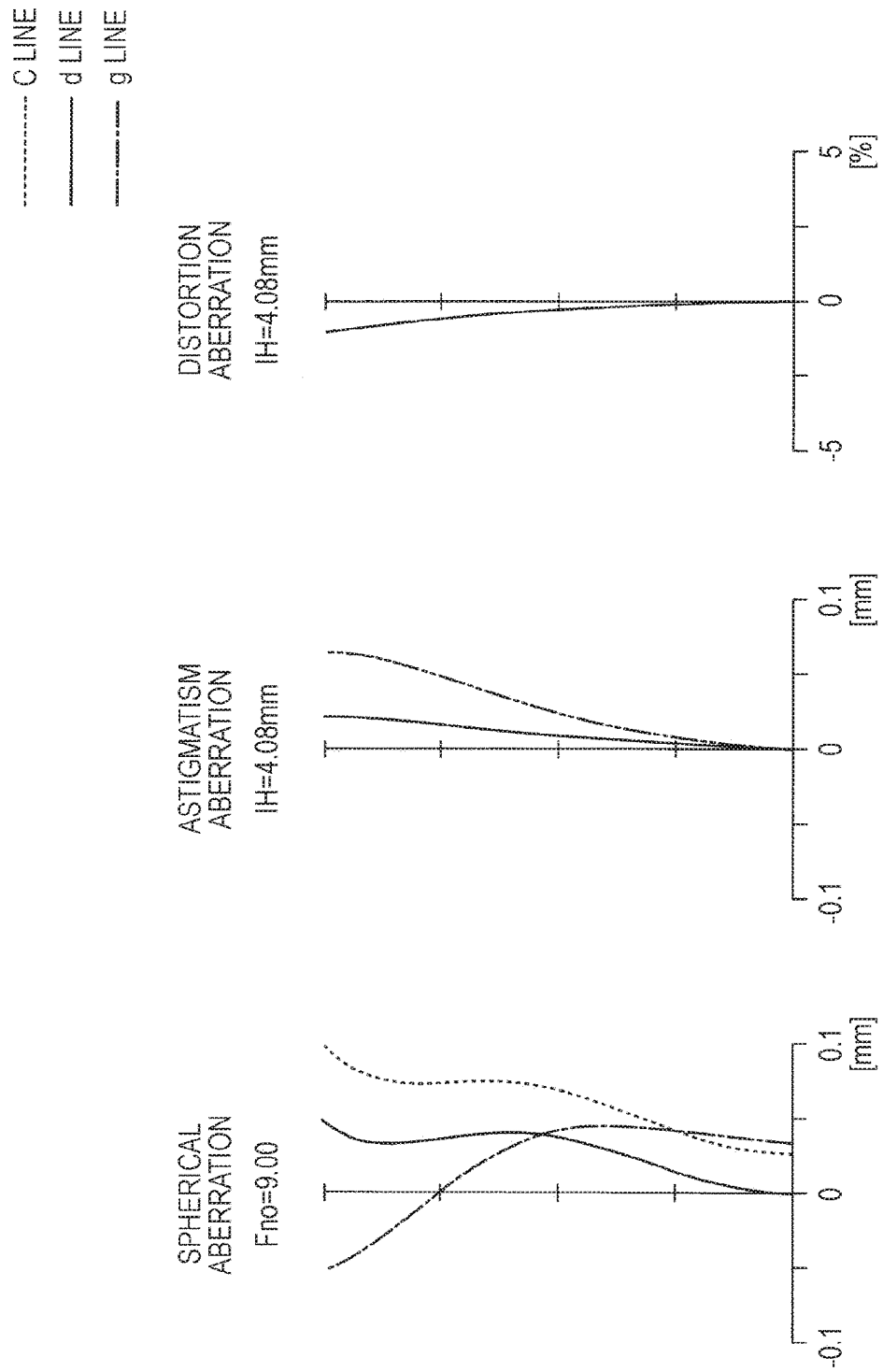
FIG. 6 is a diagram of longitudinal aberrations (spherical aberration, astigmatism aberration, and distortion aberration) at the time of focusing with an operation distance of 405 mm in a high magnification state of the numerical value example 1.
Figure 7:
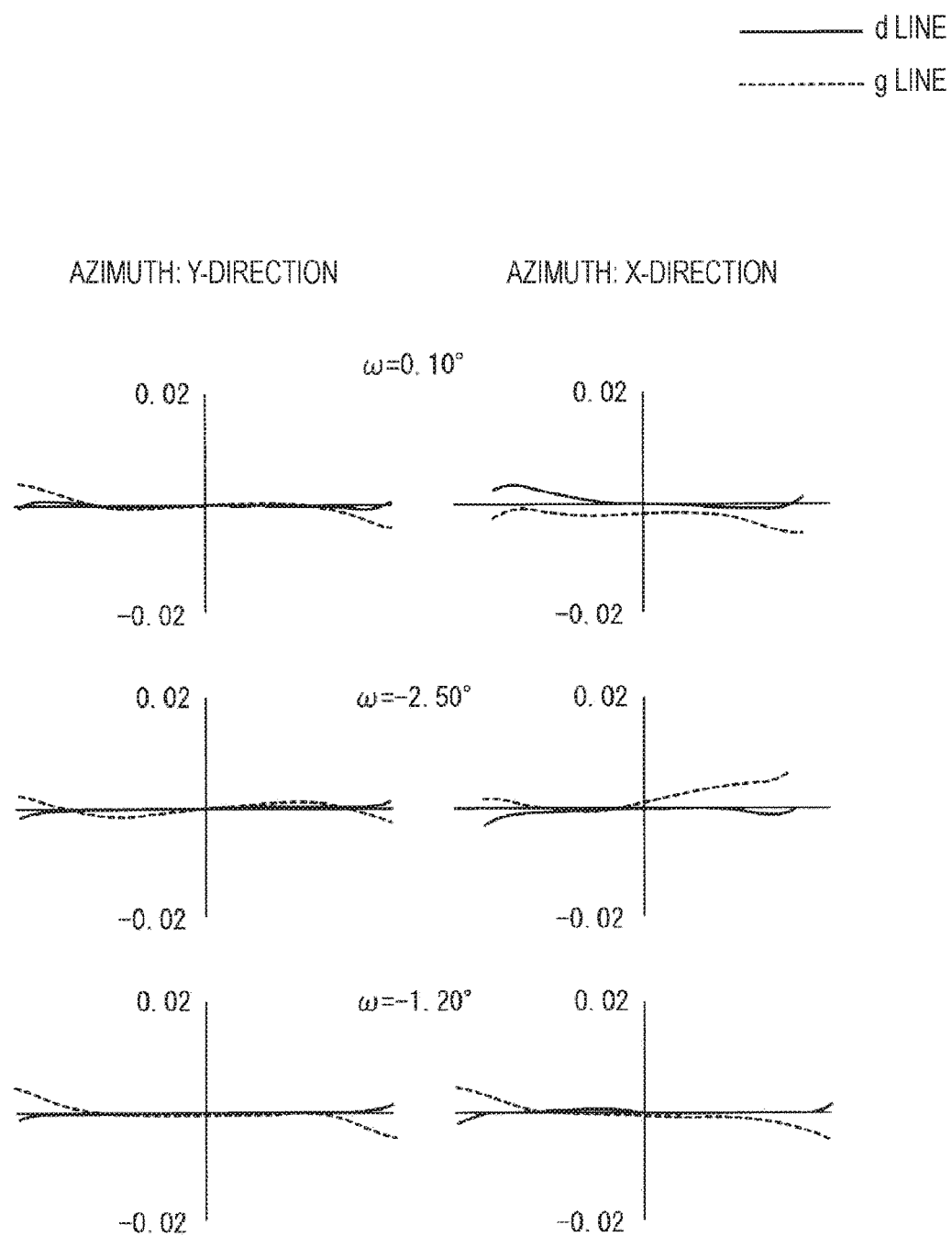
FIG. 7 is a diagram of a lateral aberration (comatic aberration) at the time of focusing with an operation distance of 405 mm in the high magnification state of the numerical value example 1.

FIGS. 2 to 7 are diagrams of various aberrations of the numerical value example 1. FIGS. 2 and 3 are diagrams of various aberrations when the operation distance is 405 mm in the low magnification state. FIGS. 4 and 5 are diagrams of various aberrations when the operation distance is 405 mm in the intermediate magnification state. FIGS. 6 and 7 are diagrams of various aberrations when the operation distance is 405 mm in the high magnification state.

Based on the diagrams of various aberrations, it is obvious that various aberrations are satisfactorily corrected and an excellent imaging performance is provided in the numerical value example 1.

Second Embodiment

Figure 8:
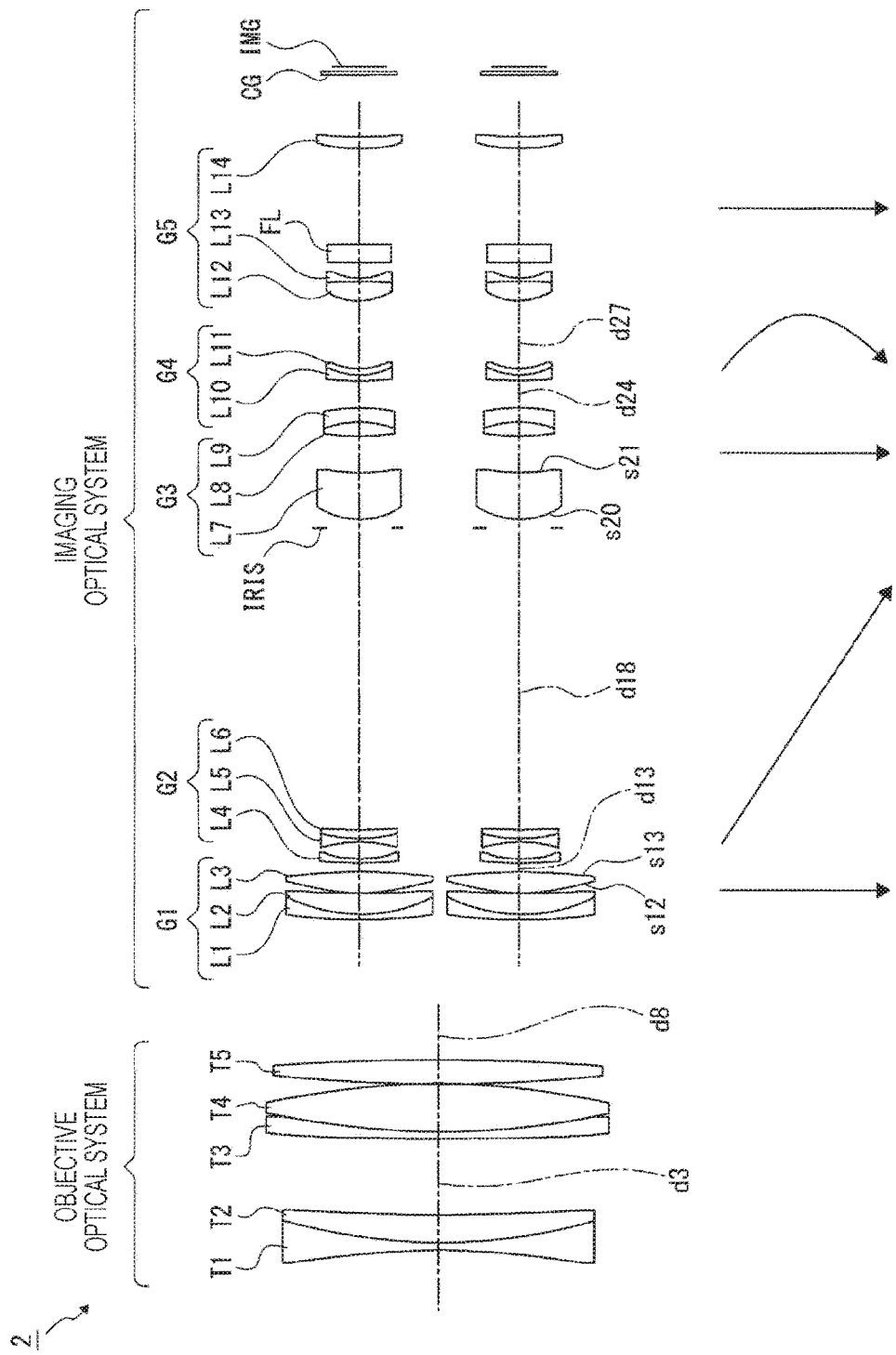
FIG. 8 is a diagram of a lens structure according to a second embodiment of a medical stereomicroscope optical system of the present technology.

FIG. 8 is a diagram of a lens structure of a medical stereomicroscope optical system 2 according to a second embodiment of the present technology.

A variable magnification ratio of the medical stereomicroscope optical system 2 is set to be about 6 times.

The objective optical system includes a compound lens formed by joining a biconcave negative lens T1 to a meniscus positive lens T2 having a convex faced to the object side, a compound lens formed by joining a meniscus negative lens T3 having a convex faced to the object side to a biconvex positive lens T4, and a biconvex positive lens T5 which are arranged in an order from the object side to the image side.

An operation distance can be changed by integrally moving the negative lens T3, the positive lens T4, and the positive lens T5 in an optical axis direction.

In the imaging optical system, an imaging optical system for a left eye is arranged at a position 10 mm eccentric relative to an optical axis of the objective optical system in an X-direction, and an imaging optical system for a right eye is arranged at a position 10 mm eccentric relative to the optical axis in the X-direction.

The imaging optical system includes a first lens group G1 having positive refractive power, a second lens group G2 having negative refractive power, a third lens group G3 having positive refractive power, a fourth lens group G4 having negative refractive power, and a fifth lens group G5 having positive refractive power which are arranged in an order from an object side to an image side. The first lens group G1, the third lens group G3, and the fifth lens group G5 are fixed lens groups which are fixed in the optical axis direction. The second lens group G2 and the fourth lens group G4 are movable lens groups which are moved in the optical axis direction.

The first lens group G1 includes a compound lens formed by joining a meniscus negative lens L1 having a convex faced to the object side to a meniscus positive lens L2 having a convex faced to the object side and a biconvex positive lens L3 which are arranged in an order from the object side to the image side.

Both surfaces of the positive lens L3 are formed as aspheric surfaces. The positive lens L3 is the aspheric surface lens so as to affect correction of a spherical aberration in a high magnification state.

The second lens group G2 includes a meniscus negative lens L4 having a convex faced to the object side and a compound lens formed by joining a biconcave negative lens L5 to a meniscus positive lens L6 having a convex faced to the object side which are arranged in an order from the object side to the image side.

The second lens group G2 simply moves from the object side to the image side when a magnification varies from the low magnification end to the high magnification end.

The third lens group G3 includes a meniscus positive lens L7 having a convex faced to the object side and a compound lens formed by joining a biconvex positive lens L8 to a meniscus negative lens L9 having a convex faced to the image side which are arranged in an order from the object side to the image side.

Both surfaces of the positive lens L7 are formed as aspheric surfaces. The positive lens L7 is the aspheric surface lens so as to affect correction of a spherical aberration in a low magnification state.

An aperture diaphragm IRIS is arranged between the second lens group G2 and the third lens group G3. The aperture diaphragm IRIS is arranged at a position close to the third lens group and is fixed in the optical axis direction.

The fourth lens group G4 includes a compound lens formed by joining a meniscus negative lens L10 having a convex faced to the object side to a meniscus positive lens L11 having a convex faced to the object side.

The fourth lens group G4 moves to the image side along the convex track when the magnification varies from the low magnification end to the high magnification end.

The fifth lens group G5 includes a compound lens formed by joining a biconvex positive lens L12 to a biconcave negative lens L13 and a meniscus positive lens L14 having a convex faced to the object side which are arranged in an order from the object side to the image side.

A filter block FL is arranged between the negative lens L13 and the positive lens L14. On the image side of the fifth lens group G5, a cover glass CG and an image surface (image pickup element) IMG are arranged in an order from the object side to the image side.

In Table 4, lens data of the numerical value example 2 obtained by applying concrete numerical values to the medical stereomicroscope optical system 2 according to the second embodiment is illustrated.

TABLE 4

| si | ri | di | ni | vi |
|---|---|---|---|---|
| OPERATION DISTANCE (WD): 405 mm ||||||
| (OBJECTIVE OPTICAL SYSTEM) |||||
| s1 | −97.0200 | 1.000 | 1.72000 | 43.7 |
| s2 | 72.2800 | 3.500 | 1.84666 | 23.8 |
| s3 | 309.7200 | VARIABLE | | |
| s4 | 216.7900 | 1.000 | 1.84666 | 23.8 |
| s5 | 102.8000 | 6.100 | 1.49700 | 81.5 |
| s6 | −85.4900 | 0.200 | | |
| s7 | 396.2000 | 2.700 | 1.53172 | 48.8 |
| s8 | −311.9000 | VARIABLE | | |
| (IMAGING OPTICAL SYSTEM) |||||
| s9 | 101.1627 | 0.700 | 1.74100 | 52.6 |
| s10 | 21.6519 | 2.679 | 1.49700 | 81.6 |
| s11 | 148.4051 | 0.150 | | |
| s12 | 29.6905 | 2.432 | 1.49710 | 81.6 |
| s13 | −82.0732 | VARIABLE | | |
| s14 | 73.8723 | 0.450 | 1.59282 | 68.6 |
| s15 | 15.0627 | 2.251 | | |
| s16 | −17.2276 | 0.400 | 1.49700 | 81.6 |
| s17 | 17.8457 | 1.143 | 1.73800 | 32.3 |
| s18 | 118.5468 | VARIABLE | | |
| s19 | INFINITY | 1.000 | | APERTURE DIAPHRAGM |
| s20 | 10.1565 | 6.000 | 1.49710 | 81.6 |
| s21 | 42.9932 | 4.512 | | |
| s22 | 35.2829 | 1.801 | 1.49700 | 81.6 |
| s23 | −10.8703 | 1.726 | 1.95375 | 32.3 |
| s24 | −22.3060 | VARIABLE | | |
| s25 | 93.9399 | 0.500 | 1.61800 | 63.4 |
| s26 | 8.3240 | 0.955 | 1.83481 | 42.7 |

TABLE 4-continued

OPERATION DISTANCE (WD): 405 mm

| si | ri | di | ni | vi |
|---|---|---|---|---|
| s27 | 11.8963 | VARIABLE | | |
| s28 | 7.9751 | 2.361 | 1.48749 | 70.4 |
| s29 | −77.0511 | 0.450 | 1.72916 | 54.7 |
| s30 | 8.4366 | 2.000 | | |
| s31 | INFINITY | 2.300 | 1.51680 | 64.2 |
| s32 | INFINITY | 12.194 | | |
| s33 | 17.8765 | 1.460 | 1.95375 | 32.3 |
| s34 | 44.9516 | 7.835 | | |
| s35 | INFINITY | 0.500 | 1.51680 | 64.2 |
| s36 | INFINITY | | | |

Amount of Eccentricity of Imaging Optical System Relative to Objective Optical System
X=10.00 Y=0.00

In the medical stereomicroscope optical system 2, both surfaces of the positive lens L3 in the first lens group G1 (twelfth and thirteenth surfaces) and both surfaces of the positive lens L7 in the third lens group G3 (twentieth and twenty-first surfaces) are formed as aspheric surfaces. The fourth order, sixth order, eighth order, and tenth order aspheric surface coefficients A4, A6, A8, and A10 of the aspheric surface in the numerical value example 2 are indicated in Table 5 together with the conic constant K.

TABLE 5

| Si | K | A4 | A6 | A8 | A10 |
|---|---|---|---|---|---|
| 12 | 0.0000 | 3.99177E−07 | −1.01640E−08 | −1.41176E−11 | 0.00000E+00 |
| 13 | 0.0000 | 1.50650E−06 | −1.42332E−08 | 0.00000E+00 | 0.00000E+00 |
| 20 | 0.0000 | 6.80777E−05 | 5.23631E−07 | 2.73458E−08 | 0.00000E+00 |
| 21 | 0.0000 | 2.60526E−04 | 1.62292E−06 | 1.11393E−07 | 0.00000E−00 |

Variable intervals of the operation distances in the low magnification state, the intermediate magnification, and the high magnification state in the numerical value example 2 are indicated in Table 6 together with the magnification and the F-number Fno.

TABLE 6

| | LOW MAGNIFICATION END | INTERMEDIATE MAGNIFICATION | HIGH MAGNIFICATION END (1) | HIGH MAGNIFICATION END (2) | HIGH MAGNIFICATION END (3) |
|---|---|---|---|---|---|
| OPERATION DISTANCE | 405.00 | 405.00 | 405.00 | 205.00 | 605.00 |
| MAGNIFICATION | 0.053 | 0.129 | 0.316 | 0.511 | 0.229 |
| Fno | 7.00 | 7.14 | 9.09 | 9.08 | 9.11 |
| d3 | 9.337 | 9.337 | 9.337 | 25.860 | 1.945 |
| d8 | 18.117 | 18.117 | 18.117 | 1.594 | 25.510 |
| d13 | 1.300 | 21.811 | 38.147 | 38.147 | 38.147 |
| d18 | 38.247 | 17.136 | 1.400 | 1.400 | 1.400 |
| d24 | 3.623 | 7.677 | 1.347 | 1.347 | 1.347 |
| d27 | 8.578 | 4.524 | 10.854 | 10.854 | 10.854 |

Figure 9:
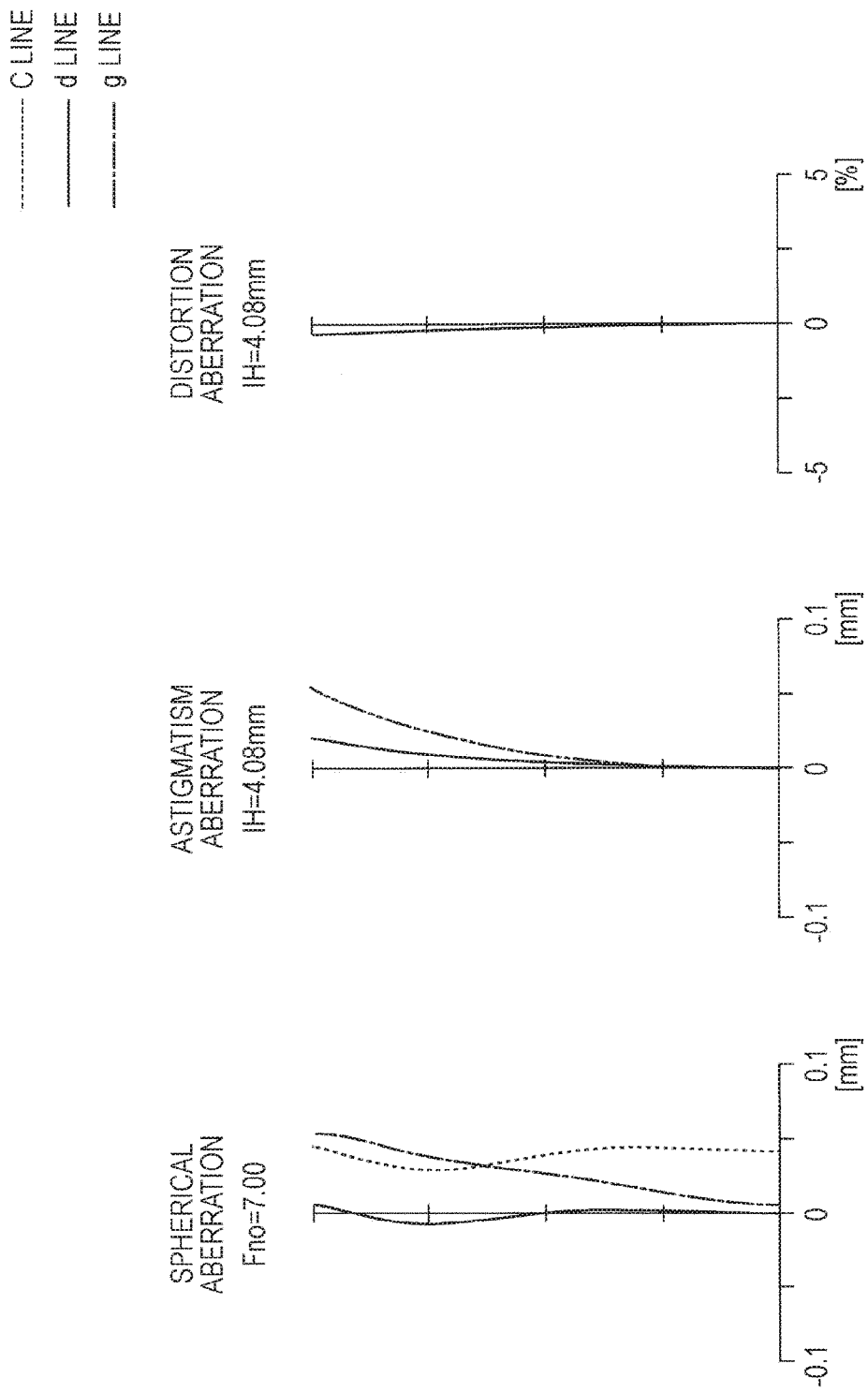
FIG. 9 illustrates aberrations in the numerical value example 2 in which concrete numerical values are applied to the second embodiment together with FIGS. 10 to 14.
Figure 10:
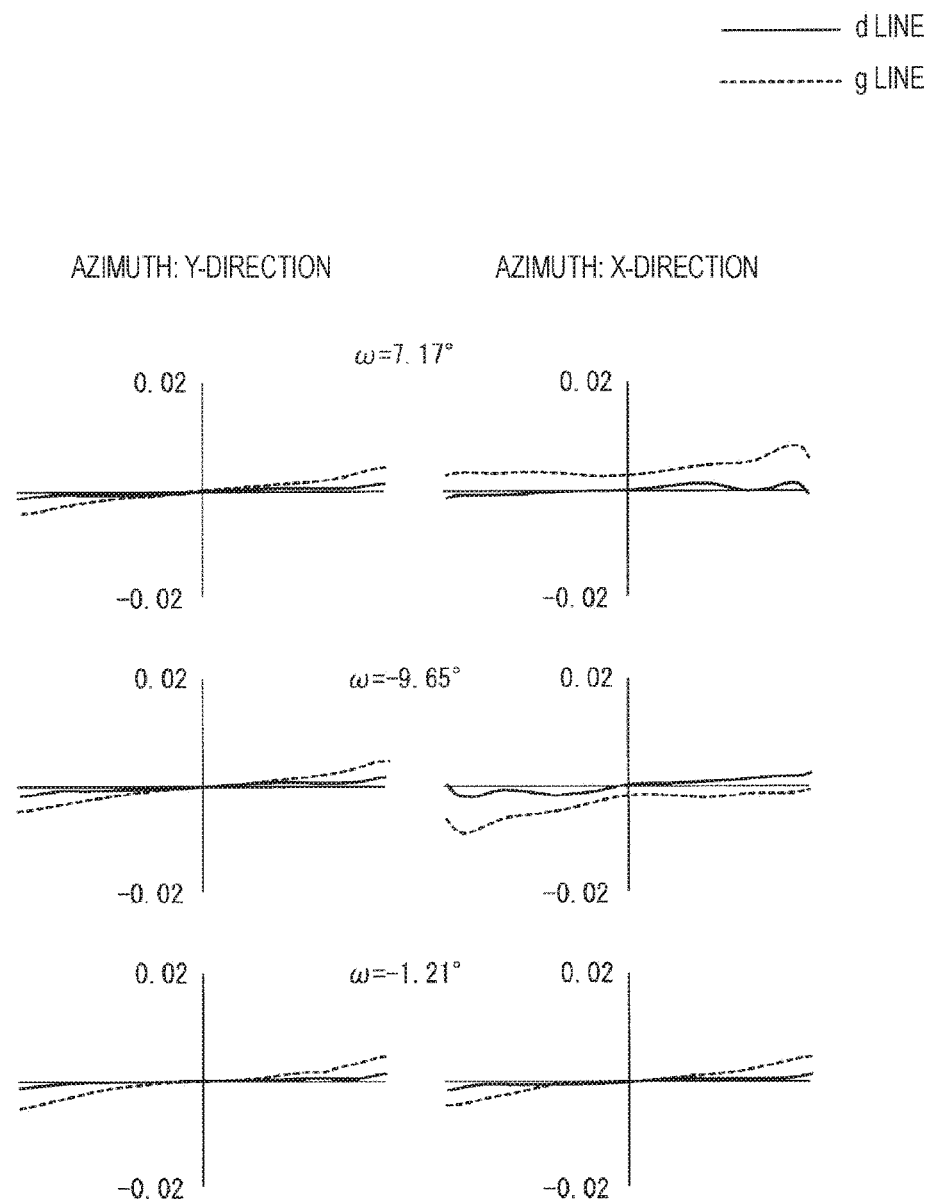
FIG. 10 is a diagram of a lateral aberration (comatic aberration) at the time of focusing with an operation distance of 405 mm in the low magnification state of the numerical value example 2.
Figure 11:
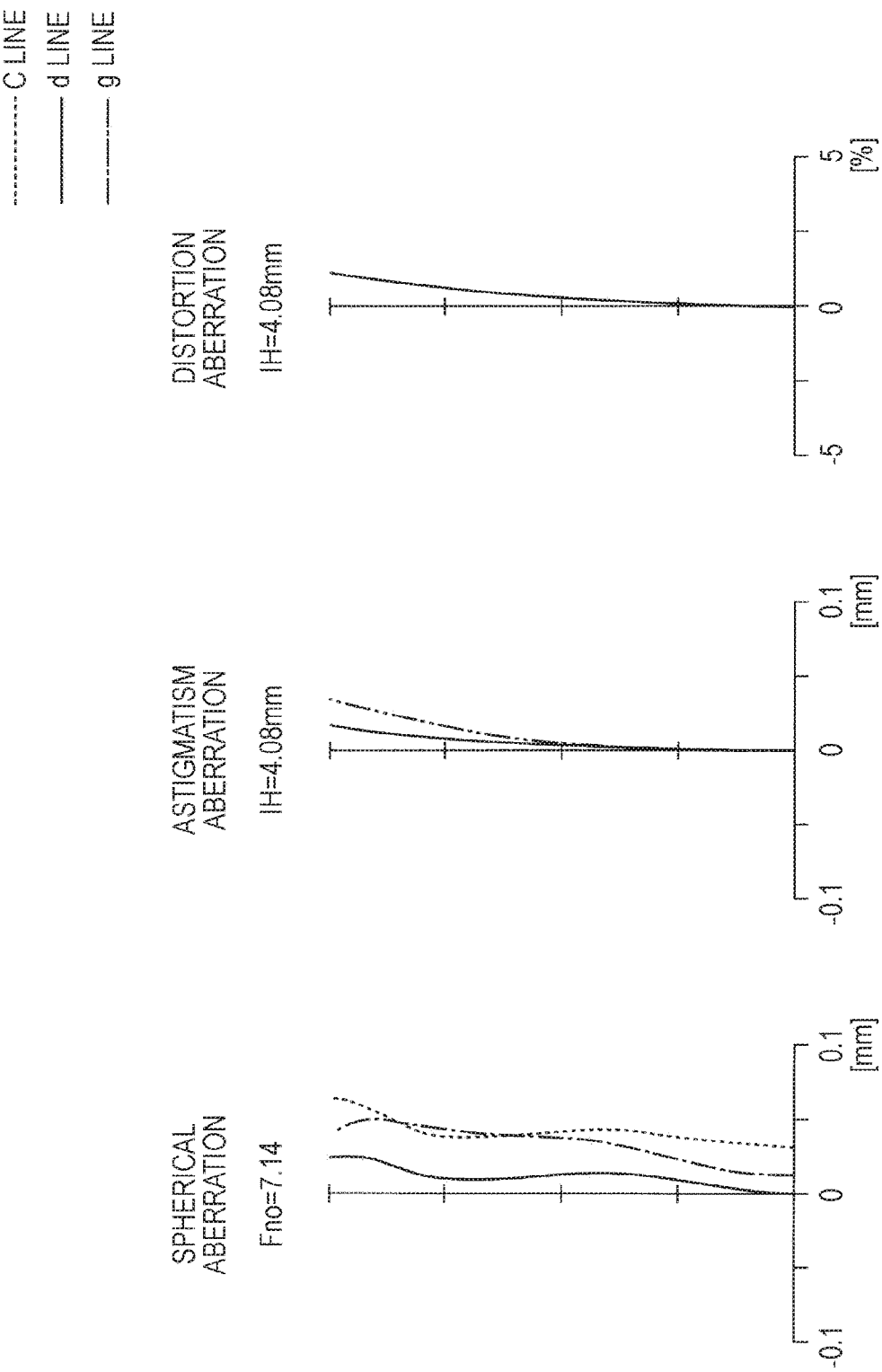
FIG. 11 is a diagram of longitudinal aberrations (spherical aberration, astigmatism aberration, and distortion aberration) at the time of focusing with an operation distance of 405 mm in the intermediate magnification state of the numerical value example 2.
Figure 12:
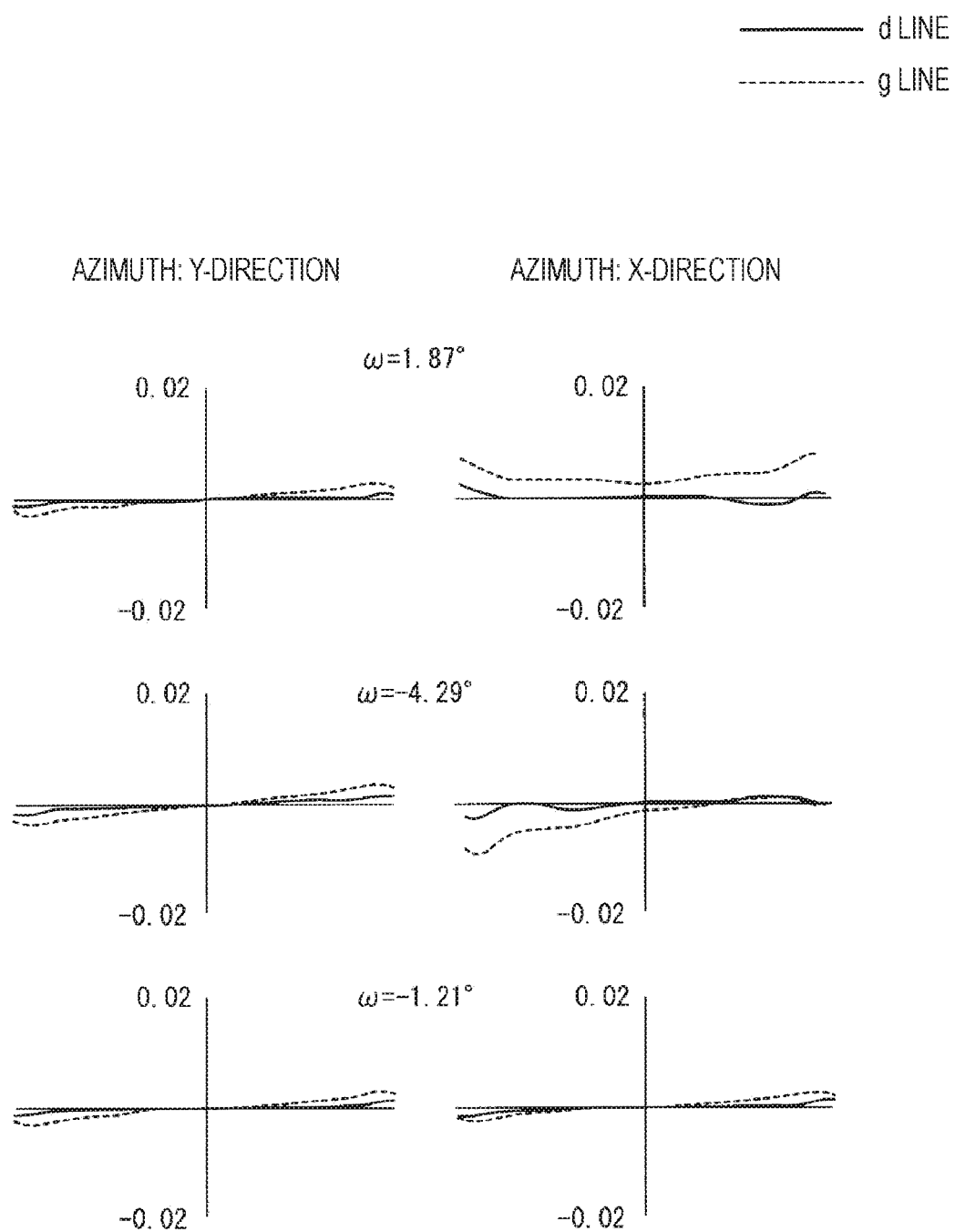
FIG. 12 is a diagram of a lateral aberration (comatic aberration) at the time of focusing with an operation distance of 405 mm in the intermediate magnification state of the numerical value example 2.
Figure 13:
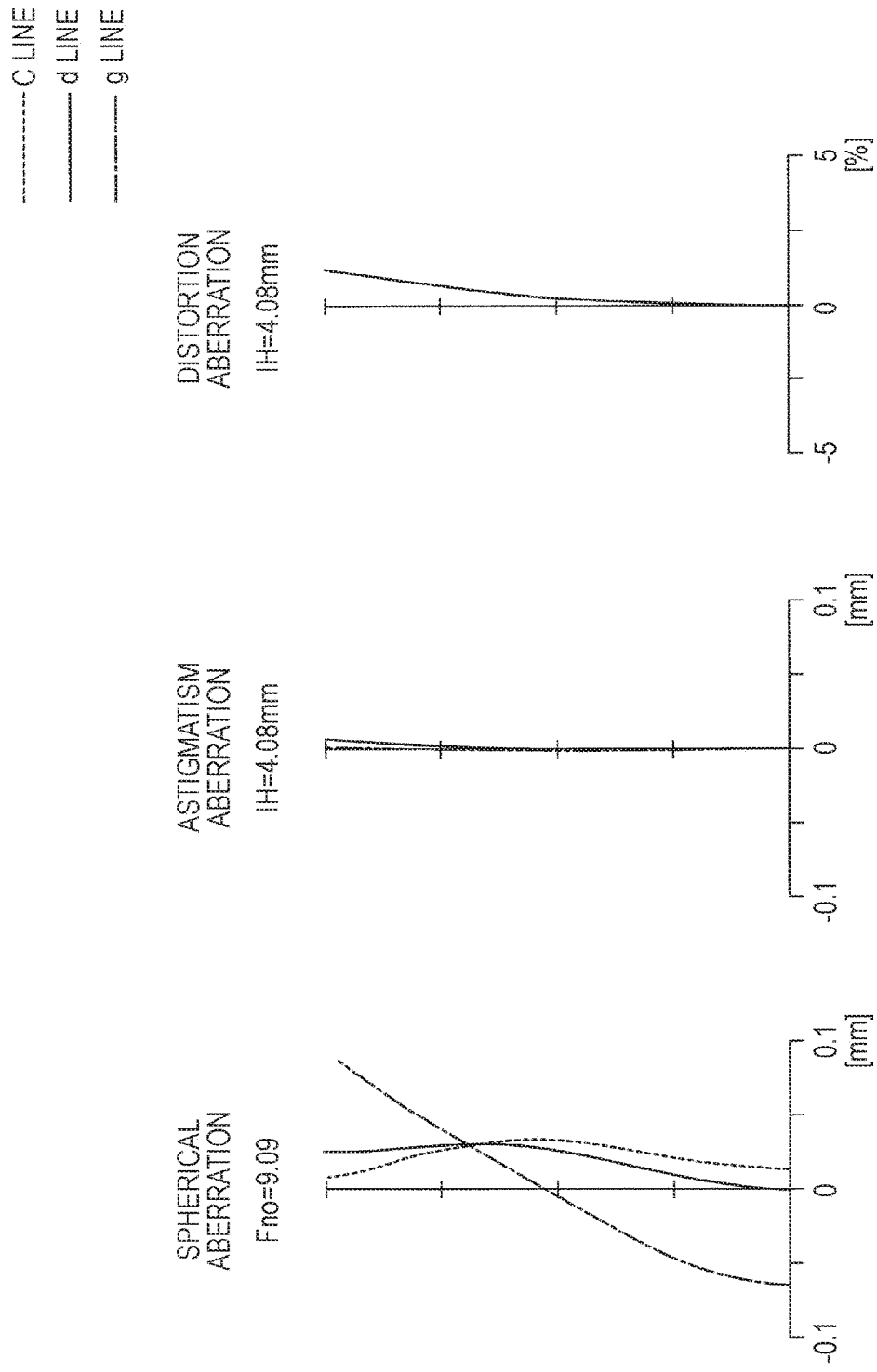
FIG. 13 is a diagram of longitudinal aberrations (spherical aberration, astigmatism aberration, and distortion aberration) at the time of focusing with an operation distance of 405 mm in the high magnification state of the numerical value example 2.
Figure 14:
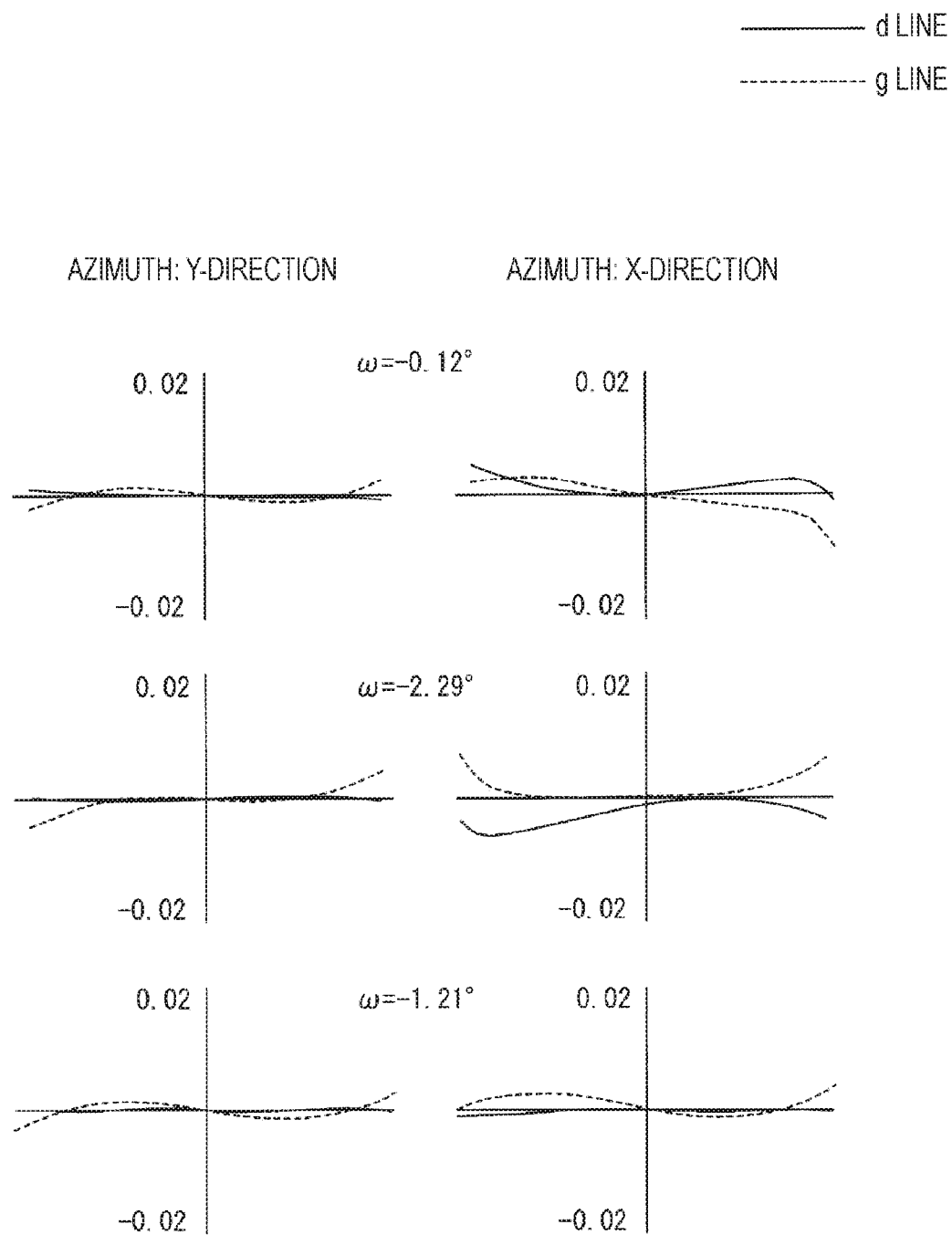
FIG. 14 is a diagram of a lateral aberration (comatic aberration) at the time of focusing with an operation distance of 405 mm in the high magnification state of the numerical value example 2.

FIGS. 9 to 14 are diagrams of various aberrations of the numerical value example 2. FIGS. 9 and 10 are diagrams of various aberrations when the operation distance is 405 mm in the low magnification state. FIGS. 11 and 12 are diagrams of various aberrations when the operation distance is 405 mm in the intermediate magnification state. FIGS. 13 and 14 are diagrams of various aberrations when the operation distance is 405 mm in the high magnification state.

Based on the diagrams of various aberrations, it is obvious that various aberrations are satisfactorily corrected and an excellent imaging performance is provided in the numerical value example 2.

[Summary of Conditional Expression]

In Table 7, values in the conditional expressions (1) to (3) of the medical stereomicroscope optical systems 1 and 2 are indicated.

TABLE 7

| CONDITIONAL EXPRESSION | NUMERICAL VALUE EXAMPLE 1 | NUMERICAL VALUE EXAMPLE 2 |
|---|---|---|
| (1) ΔFCL/IHH | 0.026 | 0.027 |
| (2) ΔFCH/IHH | 0.033 | 0.018 |
| (3) ΔDH · FnoL/IHH | 19.718 | 19.719 |
| REFERENCE | | |
| ΔFCL | 0.092 | 0.097 |
| ΔFCH | 0.116 | 0.065 |
| IHH | 3.550 | 3.550 |
| ΔDH | 10.000 | 10.000 |
| FnoL | 7.000 | 7.000 |

As it is obvious from Table 7, the medical stereomicroscope optical systems 1 and 2 satisfy the conditional expressions (1) to (3).

[Structure of Medical Observation Apparatus]

In the medical observation apparatus according to the present technology, the medical stereomicroscope optical system includes the objective optical system and the plurality of imaging optical systems which are arranged in an order from the object side to the image side and the imaging optical system has at least a single aspheric surface.

Since the imaging optical system has the aspheric surface, a spherical aberration and a field curvature can be improved, and an image quality of the small and light medical stereomicroscope optical system can be improved.

[One Embodiment of Medical Observation Apparatus]

Figure 15:
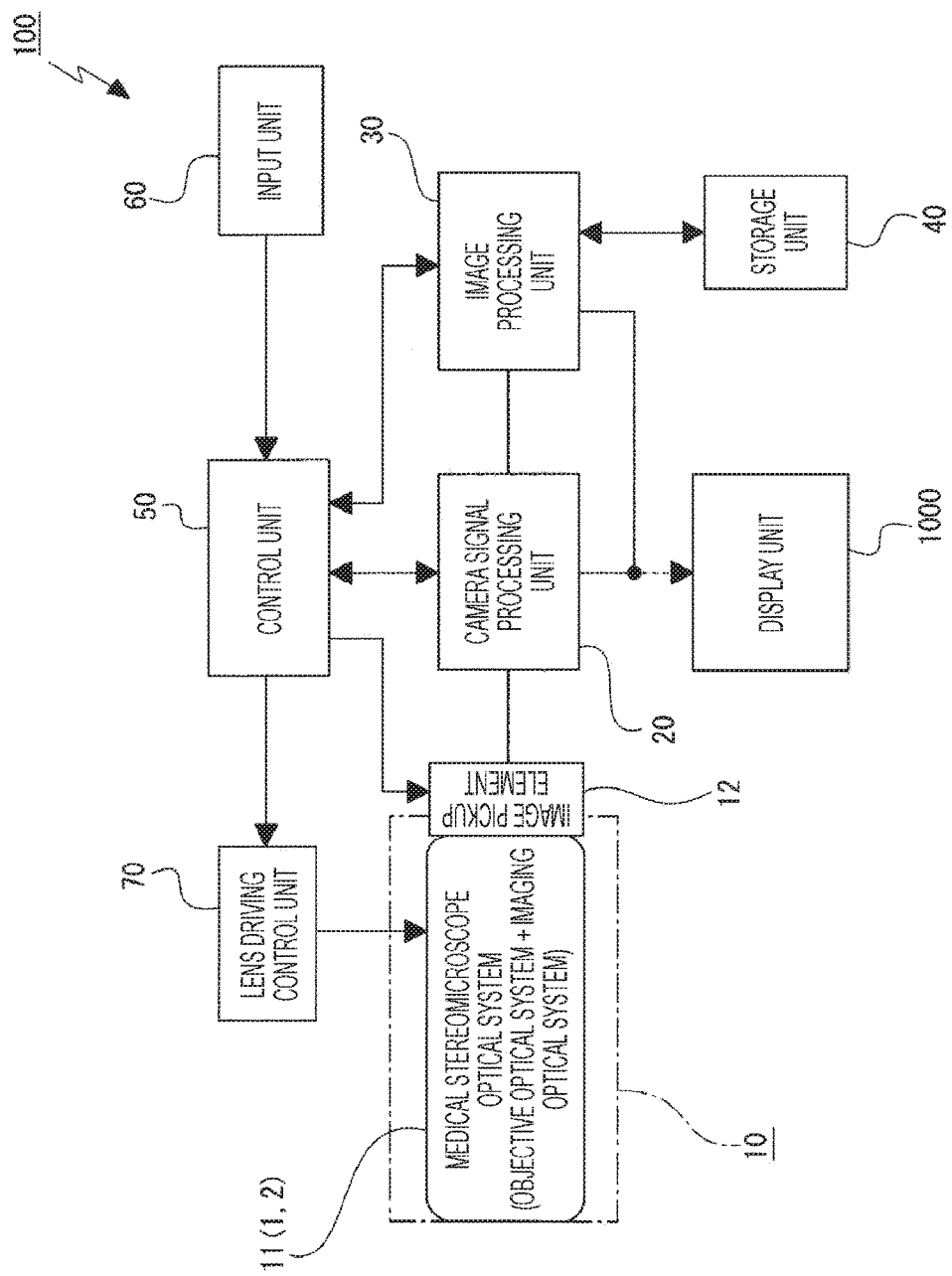
FIG. 15 is a block diagram of one embodiment of a medical observation apparatus according to the present technology.

FIG. 15 is a block diagram of one embodiment of a medical observation apparatus according to the present technology.

A medical observation apparatus 100 includes a camera block 10 which plays an imaging function, a camera signal processing unit 20 which performs signal processing such as analog/digital conversion of an imaged image signal (video signal), and an image processing unit 30 which performs recording/reproducing processing of the image signal. Also, the medical observation apparatus 100 includes a storage unit 40 such as a reader/writer (R/W) which writes and reads the image signal, a control unit 50 such as a central processing unit (CPU) which controls an entire medical observation apparatus 100, an input unit 60 configured of various switches with which a user such as an operator performs a predetermined operation, and a lens driving control unit 70 which controls the drive of lens groups arranged in the camera block 10.

The camera block 10 includes a medical stereomicroscope optical system 11 (medical stereomicroscope optical system 1 or 2 to which the present technology is applied) and an image pickup element 12 such as a charge coupled device (CCD) and a complementary metal oxide semiconductor (CMOS).

The camera signal processing unit 20 performs various signal processing to an output signal from the image pickup element 12 such as conversion into a digital signal, noise elimination, image quality correction, and conversion into a luminance and chrominance signal.

The image processing unit 30 performs compression encoding and expansion decoding processing to the image signal based on a predetermined image data format and conversion processing of a data specification such as a resolution.

The storage unit 40 writes the image data encoded by the image processing unit 30 and reads the written image data.

The control unit 50 functions as a control processing unit for controlling each circuit block provided in the medical observation apparatus 100 and controls each circuit block on the basis of an instruction input signal and the like from the input unit 60.

The input unit 60 is configured of, for example, a selection switch to select an operation mode and outputs the instruction input signal according to the operation by the user to the control unit 50.

The lens driving control unit 70 controls a motor, which is not shown, for driving each lens group of the medical stereomicroscope optical system 11 on the basis of a control signal from the control unit 50.

An operation of the medical observation apparatus 100 is described below.

At the time of imaging an image, the image signal imaged by the camera block 10 is processed by the image processing unit 30 under the control of the control unit 50 and is output to a display unit 1000 via the camera signal processing unit 20 and is displayed. The display unit 1000 is, for example, a display and a monitor which can display a stereoscopic image (stereoscopic video).

Also, when the camera block 10 is operated according to the instruction input signal from the input unit 60, the imaged image signal is output from the camera signal processing unit 20 to the image processing unit 30, and the compression encoding processing is performed to the image signal. Then, the image signal is converted into digital data having a predetermined data format. The converted data is output and written to the storage unit 40.

The image data which has been recorded in the storage unit 40 is reproduced by reading predetermined image data from the storage unit 40 according to the operation to the input unit 60 and performing the expansion decoding processing by the image processing unit 30, and after that, outputting the reproduction image signal and displaying the image, for example, on the display unit 1000.

At the time of imaging an image, the control unit 50 outputs the control signal to the lens driving control unit 70, and a predetermined lens group of the medical stereomicroscope optical system 11 is moved on the basis of the control of the lens driving control unit 70, and then, focusing and zooming are performed.

[Others]

In the medical stereomicroscope optical system according to the present technology and the medical observation apparatus according to the present technology, other optical element such as a lens which does not have refractive power may be arranged in addition to the first lens group G1 to the fourth lens group G4 or the first lens group G1 to the fifth lens group G5. In this case, the lens structure of the medical stereomicroscope optical system according to the present technology is substantially that of the four-group lens structure having the first lens group G1 to the fourth lens group G4 or that of the five-group lens structure having the first lens group G1 to the fifth lens group G5.

[The Present Technology]

The present technology can be configured as follows.

<1>

A medical stereomicroscope optical system, including:

an objective optical system and a plurality of imaging optical systems configured to be arranged in an order from an object side to an image side, wherein the imaging optical system has at least a single aspheric surface.

<2>

The medical stereomicroscope optical system according to <1>, wherein the objective optical system includes a plurality of lens groups, and an operation distance can be changed by moving a part of the lens groups of the objective optical system in an optical axis direction.

<3>

The medical stereomicroscope optical system according to <1> or <2>, wherein the imaging optical system includes a plurality of lens groups, and a variable magnification can be obtained by independently moving at least two or more lens groups of the imaging optical system in the optical axis direction while an operation distance is maintained.

<4>

The medical stereomicroscope optical system according to any one of <1> to <3>, wherein the imaging optical system includes a first lens group having positive refractive power, a second lens group having negative refractive power, a third lens group having positive refractive power, and a fourth lens group having positive refractive power which are arranged in an order from the object side to the image side, and when an image is magnified from a low magnification end to a high magnification end, the second lens group simply moves from the object side to the image side, and the third lens group moves to the image side along a convex track.

<5>
The medical stereomicroscope optical system according to <4>, wherein
an aperture diaphragm is arranged in the imaging optical system, and
the aperture diaphragm integrally moves with the third lens group.

<6>
The medical stereomicroscope optical system according to any one of <1> to <3>, wherein
the imaging optical system includes a first lens group having positive refractive power, a second lens group having negative refractive power, a third lens group having positive refractive power, a fourth lens group having negative refractive power, and a fifth lens group having positive refractive power which are arranged in an order from the object side to the image side, and
when an image is magnified from a low magnification end to a high magnification end, the second lens group simply moves from the object side to the image side, and the fourth lens group moves to the image side along a convex track.

<7>
The medical stereomicroscope optical system according to <6>, wherein
an aperture diaphragm is arranged in the imaging optical system, and
the aperture diaphragm is arranged between the second lens group and the third lens group.

<8>
The medical stereomicroscope optical system according to any one of <1> to <7>, wherein
in the imaging optical system, when it is assumed that a field curvature amount of a meridional image surface at the low magnification end with the maximum image height in the horizontal direction be ΔFCL, that a field curvature amount of a meridional image surface at the high magnification end be ΔFCH, and that the maximum image height in the horizontal direction be IHH,
the following conditional expressions (1) and (2) are satisfied.

$$0.012 < \Delta FCL/IHH < 0.050 \quad (1)$$

$$0.012 < \Delta FCH/IHH < 0.050 \quad (2)$$

<9>
The medical stereomicroscope optical system according to any one of <1> to <8>, wherein
when two imaging optical systems are provided, the two imaging optical systems are eccentrically arranged relative to the objective optical system in the horizontal direction, and
it is assumed that an absolute value of an eccentricity quantity of the imaging optical system in the horizontal direction relative to the objective optical system be ΔDH, that a F-number at the low magnification end of entire optical system be FnoL, and that the maximum image height of the imaging optical system in the horizontal direction be IHH, the following conditional expression (3) is satisfied.

$$10 < \Delta DH \cdot FnoL/IHH < 40 \quad (3)$$

<10>
The medical stereomicroscope optical system according to any one of <1> to <3>, wherein
the imaging optical system includes a first lens group having positive refractive power, a second lens group having negative refractive power, a third lens group having positive refractive power, and a fourth lens group having positive refractive power which are arranged in an order from the object side to the image side, and
the first lens group has the aspheric surface.

<11>
The medical stereomicroscope optical system according to any one of <1> to <3>, wherein
the imaging optical system includes a first lens group having positive refractive power, a second lens group having negative refractive power, a third lens group having positive refractive power, and a fourth lens group having positive refractive power which are arranged in an order from the object side to the image side, and
the third lens group has the aspheric surface.

<12>
The medical stereomicroscope optical system according to any one of <1> to <3>, wherein
the imaging optical system includes a first lens group having positive refractive power, a second lens group having negative refractive power, a third lens group having positive refractive power, a fourth lens group having negative refractive power, and a fifth lens group having positive refractive power which are arranged in an order from the object side to the image side, and
the first lens group has the aspheric surface.

<13>
The medical stereomicroscope optical system according to any one of <1> to <3>, wherein
the imaging optical system includes a first lens group having positive refractive power, a second lens group having negative refractive power, a third lens group having positive refractive power, a fourth lens group having negative refractive power, and a fifth lens group having positive refractive power which are arranged in an order from the object side to the image side, and
the third lens group has the aspheric surface.

<14>
A medical observation apparatus, including:
an objective optical system and a plurality of imaging optical systems configured to be arranged in an order from an object side to an image side; and
an image pickup element which converts an optical image formed by the objective optical system and the plurality of imaging optical systems into an electrical signal, wherein
the imaging optical system has at least a single aspheric surface.

REFERENCE SIGNS LIST 1 medical stereomicroscope optical system
2 medical stereomicroscope optical system
G1 first lens group
G2 second lens group
G3 third lens group
G4 fourth lens group
G5 fifth lens group
100 medical observation apparatus
11 medical stereomicroscope optical system
12 image pickup element

The invention claimed is:
1. A medical stereomicroscope optical system, comprising:
an objective optical system; and
a plurality of imaging optical systems in an order from an object side to an image side, wherein
each of the plurality of imaging optical systems comprises a first lens group having positive refractive power, a second lens group having negative refractive power, a third lens group having positive refractive power, and a fourth lens group having positive refractive power in an order from the object side to the image side, wherein at least one of the first lens group, the second lens group, the third lens group, and the fourth lens group has an aspheric surface, and wherein based on magnification of an image from a low magnification end to a high magnification end, the second lens group is configured to move from the object side to the image side and the third lens group is configured to move to the image side along a convex track.

2. The medical stereomicroscope optical system according to claim 1, wherein
the objective optical system includes a plurality of lens groups, and
a change in an operation distance is based on a movement of a part of the plurality of lens groups of the objective optical system in an optical axis direction.

3. The medical stereomicroscope optical system according to claim 1, wherein
at least two lens groups of the first lens group, the second lens group, the third lens group and the fourth lens group are configured to obtain the magnification based on movement of the at least two lens groups while an operation distance is constant.

4. The medical stereomicroscope optical system according to claim 1, wherein each of the plurality of imaging optical systems includes an aperture diaphragm configured to move with the third lens group.

5. The medical stereomicroscope optical system according to claim 1, wherein
each of the plurality of imaging optical systems includes the first lens group, the second lens group, the third lens group, the fourth lens group, and a fifth lens group having positive refractive power in an order from the object side to the image side, and
based on the magnification of the image from the low magnification end to the high magnification end, the fourth lens group is configured to move to the image side along the convex track.

6. The medical stereomicroscope optical system according to claim 5, wherein each of the plurality of imaging optical systems includes an aperture diaphragm between the second lens group and the third lens group.

7. The medical stereomicroscope optical system according to claim 1, wherein
in each of the plurality of imaging optical systems,
the following conditional expressions (1) and (2) are satisfied $$0.012<\Delta FCL/IHH<0.050 \tag{1}$$

$$0.012<\Delta FCH/IHH<0.050, \text{ and} \tag{2}$$

wherein $\Delta FCL$ is a field curvature amount of a meridional image surface at the low magnification end with the maximum image height in a horizontal direction, $\Delta FCH$ is a field curvature amount of the meridional image surface at the high magnification end, and IHH is the maximum image height in the horizontal direction.

8. The medical stereomicroscope optical system according to claim 1, wherein the plurality of imaging optical systems includes two imaging optical systems, each of the two imaging optical systems is eccentric relative to the objective optical system in a horizontal direction, and the following conditional expression (3) is satisfied $$10<\Delta DH\cdot FnoL/IHH<40, \tag{3}$$

wherein $\Delta DH$ is an absolute value of an eccentricity quantity of each of the two imaging optical systems in the horizontal direction relative to the objective optical system, FnoL is a F-number at the low magnification end of the two imaging optical systems, and IHH is the maximum image height of each of the two imaging optical systems in the horizontal direction.

9. The medical stereomicroscope optical system according to claim 1, wherein
the first lens group has the aspheric surface.

10. The medical stereomicroscope optical system according to claim 1, wherein
the third lens group has the aspheric surface.

11. The medical stereomicroscope optical system according to claim 1, wherein
each of the plurality of imaging optical systems includes the first lens group, the second lens group, the third lens group, the fourth lens group, and a fifth lens group having positive refractive power in an order from the object side to the image side, and
the first lens group has the aspheric surface.

12. The medical stereomicroscope optical system according to claim 1, wherein
each of the plurality of imaging optical systems includes the first lens group, the second lens group, the third lens group, the fourth lens group, and a fifth lens group having positive refractive power in an order from the object side to the image side, and
the third lens group has the aspheric surface.

13. A medical observation apparatus, comprising:
an objective optical system and a plurality of imaging optical systems in an order from an object side to an image side, wherein the objective optical system and the plurality of imaging optical systems are configured to generate an optical image; and
an image pickup element configured to convert the optical image into an electrical signal, wherein
each of the plurality of imaging optical systems comprises a first lens group having positive refractive power, a second lens group having negative refractive power, a third lens group having positive refractive power, and a fourth lens group having positive refractive power in an order from the object side to the image side,
wherein at least one of the first lens group, the second lens group, the third lens group, and the fourth lens group has an aspheric surface, and
wherein based on magnification of an image from a low magnification end to a high magnification end, the second lens group is configured to move from the object side to the image side and the third lens group is configured to move to the image side along a convex track.

* * * * *